(12) United States Patent
Ganapathy-Kanniappan et al.

(10) Patent No.: US 11,268,068 B2
(45) Date of Patent: Mar. 8, 2022

(54) IN VITRO MODEL OF METASTATIC CANCER

(71) Applicant: THE JOHNS HOPKINS UNIVERSITY, Baltimore, MD (US)

(72) Inventors: Shanmugasundaram Ganapathy-Kanniappan, Baltimore, MD (US); Rani Kunjithapatham, Chennai (IN)

(73) Assignee: The Johns Hopkins University, Baltimore, MD (US)

( * ) Notice: Subject to any disclaimer, the term of this patent is extended or adjusted under 35 U.S.C. 154(b) by 514 days.

(21) Appl. No.: 14/845,362

(22) Filed: Sep. 4, 2015

(65) Prior Publication Data

US 2016/0068817 A1 Mar. 10, 2016

Related U.S. Application Data

(60) Provisional application No. 62/046,229, filed on Sep. 5, 2014.

(51) Int. Cl.
*C12N 5/09* (2010.01)
*G01N 33/50* (2006.01)

(52) U.S. Cl.
CPC ....... *C12N 5/0693* (2013.01); *G01N 33/5008* (2013.01); *C12N 2503/02* (2013.01); *C12N 2513/00* (2013.01); *C12N 2533/50* (2013.01)

(58) Field of Classification Search
CPC .............. C12N 5/0693; C12N 2503/02; C12N 2513/00; G01N 33/5008
See application file for complete search history.

(56) References Cited

PUBLICATIONS

Pease et al., Biology Open, 2012, vol. 1, pp. 622-628.*
Guttilla et al., Prolonged mammosphere culture of MCF-7 cells induces an EMT and repression of the estrogen receptor by microRNAs. Breast Cancer Research and Treatment, vol. 132 (2012) pp. 75-85. (Year: 2012).*
Sethi, N. & Kang, Y. Unravelling the complexity of metastasis—molecular understanding and targeted therapies. Nat. Rev. Cancer. 11, 735-748 (2011).
Francia, G., Cruz-Munoz, W., Man, S., Xu, P. & Kerbel, R. S. Mouse models of advanced spontaneous metastasis for experimental therapeutics. Nat. Rev. Cancer. 11, 135-141 (2011).
Nguyen, D. X., Bos, P. D. & Massague, J. Metastasis: from dissemination to organ-specific colonization. Nat. Rev. Cancer. 9, 274-284 (2009).
Albini, A. et al. A rapid in vitro assay for quantitating the invasive potential of tumor cells. Cancer Res. 47, 3239-3245 (1987).
Hirschhaeuser, F. et al. Multicellular tumor spheroids: an underestimated tool is catching up again. J. Biotechnol. 148, 3-15 (2010).
Liao, J. et al. Ovarian cancer spheroid cells with stem cell-like properties contribute to tumor generation, metastasis and chemotherapy resistance through hypoxia-resistant metabolism. PLoS One 9, e84941 (2014).
Harunaga, J. S. & Yamada, K. M. Cell-matrix adhesions in 3D. Matrix Biol. 30, 363-368 (2011).
Ma, S., Lee, T. K., Zheng, B. J., Chan, K. W. & Guan, X. Y. CD133+ HCC cancer stem cells confer chemoresistance by preferential expression of the Akt/PKB survival pathway. Oncogene 27, 1749-1758 (2008).
Richardson, G. D. et al. CD133, a novel marker for human prostatic epithelial stem cells. J. Cell. Sci. 117, 3539-3545 (2004).
Hermann, P. C. et al. Distinct populations of cancer stem cells determine tumor growth and metastatic activity in human pancreatic cancer. Cell. Stem Cell. 1, 313-323 (2007).
Krohn, A. et al. CXCR4 receptor positive spheroid forming cells are responsible for tumor invasion in vitro. Cancer Lett. 280, 65-71 (2009).
Hu, L. et al. Association of Vimentin overexpression and hepatocellular carcinoma metastasis. Oncogene 23, 298-302 (2004).
Mani, S. A. et al. The epithelial-mesenchymal transition generates cells with properties of stem cells. Cell 133, 704-715 (2008).
Elshamy, W. M. & Duhe, R. J. Overview: cellular plasticity, cancer stem cells and metastasis. Cancer Lett. 341, 2-8 (2013).
Thiery, J. P. Epithelial-mesenchymal transitions in tumour progression. Nat. Rev. Cancer. 2, 442-454 (2002).
Kimlin, L. C., Casagrande, G. & Virador, V. M. In vitro three-dimensional (3D) models in cancer research: an update. Mol. Carcinog. 52, 167-182 (2013).
Ray, P., De, A., Min, J. J., Tsien, R. Y. & Gambhir, S. S. Imaging tri-fusion multimodality reporter gene expression in living subjects. Cancer Res. 64, 1323-1330 (2004).
Ganapathy-Kanniappan, S. et al. Human hepatocellular carcinoma in a mouse model: assessment of tumor response to percutaneous ablation by using glyceraldehyde-3-phosphate dehydrogenase antagonists. Radiology 262, 834-845 (2012).
Neuhoff, V., Arold, N., Taube, D. & Ehrhardt, W. Improved staining of proteins in polyacrylamide gels including isoelectric focusing gels with clear background at nanogram sensitivity using Coomassie Brilliant Blue G-250 and R-250. Electrophoresis 9, 255-262 (1988).
Kunjithapatham et al (2014) Reversal of anchorage-independent multicellular spheroid into a monolayer mimics a metastatic model. Sci Rep. Oct. 29, 2014;4:6816. doi: 10.1038/srep06816.

(Continued)

*Primary Examiner* — Kara D Johnson
(74) *Attorney, Agent, or Firm* — Johns Hopkins Technology Ventures

(57) ABSTRACT

The present invention relates to drug discovery and development. More specifically, the present invention provides methods and composition useful for screening anti-cancer agents. In a specific embodiment, a method for screening candidate anti-cancer agents comprises the steps of (a) contacting a monolayer of reversible spheroid cancer cells with a candidate anti-cancer agent; and (b) measuring the response of the reversible spheroid cancer cells to the candidate anti-cancer agent.

3 Claims, 14 Drawing Sheets

Specification includes a Sequence Listing.

(56) References Cited

PUBLICATIONS

Shield et al (2009) Multicellular spheroids in ovarian cancer metastases: Biology and pathology. Gynecol Oncol. Apr. 2009;113(1):143-8. doi: 10.1016/j.ygyno.2008.11.032. Epub Jan. 10, 2009.

Sutherland et al (1971) Growth of multicell spheroids in tissue culture as a model of nodular carcinomas. J Natl Cancer Inst. Jan. 1971;46(1):113-20.

Friedrich et al (2009) Spheroid-based drug screen: considerations and practical approach. Nat Protoc. 2009;4(3):309-24. doi: 10.1038/nprot.2008.226. Epub Feb. 12, 2009.

Desoize et al (2000) Contribution of three-dimensional culture to cancer research. Crit Rev Oncol Hematol. Nov.-Dec. 2000;36(2-3):59-60.

Desoize et al (2000) Multicellular resistance: a paradigm for clinical resistance? Crit Rev Oncol Hematol. Nov.-Dec. 2000;36(2-3):193-207.

Gomes et al (2015) Three-dimensional microenvironment confers enhanced sensitivity to doxorubicin by reducing p53-dependent induction of autophagy. Oncogene. Oct. 16, 2015;34(42):5329-40. doi: 10.1038/onc.2014.461. Epub Jan. 26, 2015.

Hoshida et al (2007) Gene expressions associated with chemosensitivity in human hepatoma cells. Hepatogastroenterology. Mar. 2007;54(74):489-92.

Muller et al (1997) Drug-induced apoptosis in hepatoma cells is mediated by the CD95 (APO-1/Fas) receptor/ligand system and involves activation of wild-type p53. J Clin Invest. Feb. 1, 1997;99(3):403-13.

Hanahan et al (2011) Hallmarks of cancer: the next generation. Cell. Mar. 4, 2011;144(5):646-74. doi: 10.1016/j.cell.2011.02.013.

Ganapathy-Kanniappan et al (2013) Tumor glycolysis as a target for cancer therapy: progress and prospects. Mol Cancer. Dec. 3, 2013;12:152. doi: 10.1186/1476-4598-12-152.

* cited by examiner

SEQUENCE LISTING

```
<160> NUMBER OF SEQ ID NOS: 20

<210> SEQ ID NO 1
<211> LENGTH: 20
<212> TYPE: DNA
<213> ORGANISM: Artificial Sequence
<220> FEATURE:
<223> OTHER INFORMATION: ALDH1A1 forward primer

<400> SEQUENCE: 1
ttgttcctgg ttatgggcct                                              20

<210> SEQ ID NO 2
<211> LENGTH: 20
<212> TYPE: DNA
<213> ORGANISM: Artificial Sequence
<220> FEATURE:
<223> OTHER INFORMATION: ALDH1A1 reverse primer

<400> SEQUENCE: 2
tccagtttgg ccccttcttt                                              20

<210> SEQ ID NO 3
<211> LENGTH: 20
<212> TYPE: DNA
<213> ORGANISM: Artificial Sequence
<220> FEATURE:
<223> OTHER INFORMATION: EPCAM forward primer

<400> SEQUENCE: 3
taaaagtttg cggactgcac                                              20

<210> SEQ ID NO 4
<211> LENGTH: 20
<212> TYPE: DNA
<213> ORGANISM: Artificial Sequence
<220> FEATURE:
```

<223> OTHER INFORMATION: EPCAM reverse primer

<400> SEQUENCE: 4
gccacatcag ctatgtccac                                        20

<210> SEQ ID NO 5
<211> LENGTH: 20
<212> TYPE: DNA
<213> ORGANISM: Artificial Sequence
<220> FEATURE:
<223> OTHER INFORMATION: PROM1 forward primer

<400> SEQUENCE: 5
cctctggtgg ggtatttctt                                        20

<210> SEQ ID NO 6
<211> LENGTH: 20
<212> TYPE: DNA
<213> ORGANISM: Artificial Sequence
<220> FEATURE:
<223> OTHER INFORMATION: PROM1 reverse primer

<400> SEQUENCE: 6
cagtttccga ctccttttga                                        20

<210> SEQ ID NO 7
<211> LENGTH: 20
<212> TYPE: DNA
<213> ORGANISM: Artificial Sequence
<220> FEATURE:
<223> OTHER INFORMATION: THY1 forward primer

<400> SEQUENCE: 7
aggaagcctc aagttccagt                                        20

<210> SEQ ID NO 8
<211> LENGTH: 20
<212> TYPE: DNA
<213> ORGANISM: Artificial Sequence
<220> FEATURE:
<223> OTHER INFORMATION: THY1 reverse primer

<400> SEQUENCE: 8
aaaagacagc cagaggtgtg                                        20

<210> SEQ ID NO 9
<211> LENGTH: 20
<212> TYPE: DNA
<213> ORGANISM: Artificial Sequence
<220> FEATURE:
<223> OTHER INFORMATION: CXCR4 forward primer

<400> SEQUENCE: 9
ggtggtctat gttggcgtct                                        20

<210> SEQ ID NO 10
<211> LENGTH: 20
<212> TYPE: DNA
<213> ORGANISM: Artificial Sequence
<220> FEATURE:
<223> OTHER INFORMATION: CXCR4 reverse primer

<400> SEQUENCE: 10
tggagtgtga cagcttggag                                        20

```
<210> SEQ ID NO 11
<211> LENGTH: 20
<212> TYPE: DNA
<213> ORGANISM: Artificial Sequence
<220> FEATURE:
<223> OTHER INFORMATION: NANOG forward primer

<400> SEQUENCE: 11
acctacctac cccagccttt                                               20

<210> SEQ ID NO 12
<211> LENGTH: 20
<212> TYPE: DNA
<213> ORGANISM: Artificial Sequence
<220> FEATURE:
<223> OTHER INFORMATION: NANOG reverse primer

<400> SEQUENCE: 12
catgcaggac tgcagagatt                                               20

<210> SEQ ID NO 13
<211> LENGTH: 20
<212> TYPE: DNA
<213> ORGANISM: Artificial Sequence
<220> FEATURE:
<223> OTHER INFORMATION: ABCG2 forward primer

<400> SEQUENCE: 13
taaagtggca gactccaagg                                               20

<210> SEQ ID NO 14
<211> LENGTH: 20
<212> TYPE: DNA
<213> ORGANISM: Artificial Sequence
<220> FEATURE:
<223> OTHER INFORMATION: ABCG2 reverse primer

<400> SEQUENCE: 14
ttgttcgtcc ctgcttagac                                               20

<210> SEQ ID NO 15
<211> LENGTH: 20
<212> TYPE: DNA
<213> ORGANISM: Artificial Sequence
<220> FEATURE:
<223> OTHER INFORMATION: CDH12 forward primer

<400> SEQUENCE: 15
tggatggacc ttatgttgct                                               20

<210> SEQ ID NO 16
<211> LENGTH: 20
<212> TYPE: DNA
<213> ORGANISM: Artificial Sequence
<220> FEATURE:
<223> OTHER INFORMATION: CDH12 reverse primer

<400> SEQUENCE: 16
aacacctgtc ttgggatcaa                                               20

<210> SEQ ID NO 17
<211> LENGTH: 20
<212> TYPE: DNA
<213> ORGANISM: Artificial Sequence
<220> FEATURE:
<223> OTHER INFORMATION: SNAI1 forward primer
```

```
<400> SEQUENCE: 17
accccacatc cttctcactg                                          20

<210> SEQ ID NO 18
<211> LENGTH: 20
<212> TYPE: DNA
<213> ORGANISM: Artificial Sequence
<220> FEATURE:
<223> OTHER INFORMATION: SNAI1 reverse primer

<400> SEQUENCE: 18
tacaaaaacc cacgcagaca                                          20

<210> SEQ ID NO 19
<211> LENGTH: 20
<212> TYPE: DNA
<213> ORGANISM: Artificial Sequence
<220> FEATURE:
<223> OTHER INFORMATION: TAGLN forward primer

<400> SEQUENCE: 19
gcagtccaaa atcgagaaga                                          20

<210> SEQ ID NO 20
<211> LENGTH: 20
<212> TYPE: DNA
<213> ORGANISM: Artificial Sequence
<220> FEATURE:
<223> OTHER INFORMATION: TAGLN reverse primer

<400> SEQUENCE: 20
accagcttgc tcagaatcac                                          20
```

IN VITRO MODEL OF METASTATIC CANCER

CROSS-REFERENCE TO RELATED APPLICATIONS

This application claims the benefit of U.S. Provisional Application No. 62/046,229, filed Sep. 5, 2014, which is incorporated herein by reference in its entirety.

FIELD OF THE INVENTION

The present invention relates to drug discovery and development. More specifically, the present invention provides methods and compositions useful for screening anti-cancer agents.

INCORPORATION-BY-REFERENCE OF MATERIAL SUBMITTED ELECTRONICALLY

This application contains a sequence listing. It has been submitted electronically via EFS-Web as an ASCII text file entitled "P13089-02_ST25.txt." The sequence listing is 6,003 bytes in size, and was created on Sep. 4, 2015. It is hereby incorporated by reference in its entirety.

BACKGROUND OF THE INVENTION

Cancer-related high mortality rate and poor prognosis are often attributed to the aggressive phenotype known as metastasis. Although our understanding on the process of metastasis has significantly advanced in the recent past, the development of an effective therapeutic for metastasis remains elusive. Identification of a sensitive molecular target requires a detailed characterization of the regulatory networks of metastatic-cascade. This in turn relies on an ideal in vitro model that represents all the known properties of metastatic cancer. Current metastatic models rely to a great degree on in vivo methods such as intraperitoneal, intravenous or subcutaneous delivery of cancer cells followed by the investigation of tumorigenesis at distal organs. These methodologies are very useful to characterize the tumorigenic potential of cancer cells and the nature of microenvironment that facilitates tumor formation. However, these approaches circumvent or evade the key features of metastatic cascade such as invasion, migration, and epithelial-mesenchymal transition (EMT). Due to the omission of such initial steps of metastatic cascade it is plausible that potential molecular targets that are critical for the metastatic phenotype may be missed.

On the other hand, in vitro models to mimic metastasis largely rely upon the "Boyden chamber" design, and several modifications of it, which demonstrate the invasion of cancer cells. Although the assay in general represents one of the salient features of metastasis, it relies heavily on local-invasion which doesn't depend on EMT and cancer-stemness/tumorigenic potential that are frequently witnessed in metastatic cells. A recent development in the creation of an in vitro system is the generation of three dimensional (3D) culture with the aid of extracellular matrix (ECM) or ECM-like materials that facilitate cellular aggregation and prevent attachment of cells to the adhesive-basement of the culture vessel. Such 3D cultures, also referred as multicellular spheroids (MCS), provide many advantages over the conventional 2D culture (monolayer). From the metastasis perspective, although, the 3D architecture mimics the in vivo tumor and has been known to possess cancer stem cell markers and the "potential" for metastasis, the manifestation of metastatic phenotype remains unclear. Recently, it has been demonstrated that human cancer cells in 3D-culture are more sensitive to doxorubicin (a clinically used anticancer drug) than its corresponding monolayer culture. This indicates that under experimental conditions the microenvironment of 3D culture could make cancer cells more sensitive than expected resistance. This could eventually mislead the identification of a fallacious compound as potential anticancer agent that may be less-effective under clinical conditions. Furthermore, potential concerns and technical issues related to the adhesion-complexes of 3D culture and their impact on the biology of cancer cells have also been reviewed. Thus there is a critical need for an ideal in vitro model that represents distinctive features of metastasis such as migration/invasion, chemoresistance and cancer stem cell-like potential.

SUMMARY OF THE INVENTION

The present invention is based, at least in part, on the development of a framework to improve the drug screening efficiency against cancer, especially, against the resistant or aggressive phenotype. The present invention provides a modified in vitro system that involves a two-step cell culture procedure before initiating any drug screening. The method includes (1) isolation of anchorage-independent, spheroid forming cells and (2) reversing the spheroids into monolayer cells (referred here-in as "reversed-spheroids" and abbreviated as "rs"). The primary modification is that the spheroids were created solely based on the anchorage-independence using ultra-low attachment culture conditions, and not using any chemical agents, such as matrigel or EDTA, linkers etc. In addition, the spheroids thus generated were further tested for their capacity to form monolayer and vice versa. See FIG. 2.

Thus, the present invention allows isolation and enrichment of cancer cells with aggressive/survival phenotype based on anchorage-independence for further downstream application such as drug screening. The generation of spheroids does not involve any chemical addition (gel, linkers, EDTA etc.) or manipulation (constant shaking in rotator shaker), avoiding their interference in cell physiology. Spheroids are selected based on their survival capacity under unfavorable (anchorage-independence) growth condition, a key feature of metastatic/aggressive phenotypic cells. Notably, because anchorage independent growth is known as an innate property of cancer stem or stem-like cells, drug screening could be performed against an aggressive phenotype which is responsible for the tumor recurrence. This is critical to circumvent the major challenge, i.e., tumor recurrence, often contributed by the cancer stem or stem-like cells. Thus, drug screening against such anchorage-independent cells (which include cancer stem-like cell phenotype) will enable researchers to target cancer stem cells for the complete eradication of cancer. Testing against the aggressive reversible spheroid monolayer cells in two-dimensional set-up would prevent/avoid the concern of drug penetration under a three-dimensional (physical) architecture. Thus, any resistance that is witnessed against any anticancer agent could be interpreted as due to the innate-property (i.e., chemoresistance) of the cells.

Accordingly, in one aspect, the present invention provides methods for preparing cancer cells for drug screening. In one embodiment, a method for preparing cancer cells for in vitro drug screening comprises the steps of (a) culturing the cancer cells under non-adhesive conditions to produce spheroid cells; (b) isolating the spheroid cells; and (c) culturing the spheroid cells under adhesive conditions to reverse the spheroid cells into monolayer cells. In another embodiment, a method for testing the response of cancer cells to exposure with at least one therapeutic agent comprises the steps of (a) culturing the cancer cells under non-adhesive conditions to produce spheroid cells; (b) isolating the spheroid cells; (c) culturing the spheroid cells under adhesive conditions to reverse the spheroid cells into monolayer cells; (d) contacting the reversed spheroid cells with at least one therapeutic agent; and (e) measuring the response of the reversed spheroid cells to the at least one therapeutic agent. In such embodiments, the culturing step to produce spheroid cells is performed without gel-like substances or chemical chelating agents that promote spheroid formation. Such agents promote spheroid formation, for example, by aggregation irrespective of their colony-forming capacity or anchorage-independent growth.

In another embodiment, the present invention provides a method for preparing reversible spheroid cancer cells useful in drug screening comprising the steps of (a) culturing adherent cancer cells under non-adhesive conditions sufficient to form spheroid cells; and (b) culturing the spheroid cells under adhesive conditions to reverse the spheroid cells into monolayer cells. In a more specific embodiment, a method for screening candidate anti-cancer agents comprises the steps of (a) contacting reversible spheroid cells with a candidate anti-cancer agent; (b) contacting the adherent cancer cells with the same candidate anti-cancer agent; and (c) measuring the response of the reversible spheroid cells and the adherent cancer cells to the candidate anti-cancer agent.

The present invention also provides reversible spheroid cells produced by the methods described herein. In another aspect, the present invention provides methods for screening anti-cancer agents. In a specific embodiment, a method for screening candidate anti-cancer agents comprises the steps of (a) contacting a monolayer of reversible spheroid cancer cells with a candidate anti-cancer agent; and (b) measuring the response of the reversible spheroid cancer cells to the candidate anti-cancer agent. In another embodiment, the method further comprises (c) contacting the parent cancer cells from which the reversible cancer cells were derived with a candidate anti-cancer agent; (d) measuring the response of the parent cancer cells to the candidate anti-cancer agent. In certain embodiments, the culturing step to produce spheroid cells is performed without gel-like substances or chemical chelating agents that promote spheroid formation.

Furthermore, as described herein, the compositions and methods of the present invention can be used as an in vitro cancer stem-cell like model to test anti-cancer drug resistance. In such embodiments, the methods can utilize the biomarkers described herein. In further embodiments, the present invention provides substrates (e.g., plates) comprising aggressive cancer cells including, for example, monolayers of such cells. The cells in such embodiments can be transfected with reporters as described herein and can include luciferase and G418 components.

BRIEF DESCRIPTION OF THE FIGURES

(FIG. 1A) The parental cell line, Huh7 as monolayer. (FIGS. 1B, 1C) Anchorage-independent growth of multicellular spheroids shown at low (1B) and high magnifications (1C). (FIGS. 1D-1F) Induction of reversal of a spheroid into monolayer at increasing magnifications. (FIG. 1G) Progressive reversal of a spheroid over few days to reach complete reversal.

FIG. 2A: A schematic showing current in vitro models and the proposed in vitro model. White color represents proliferative cells, black color indicates resistant or aggressive phenotypic cells. FIG. 2B: upregulation of metastatic genes in rs-monolayer population. qPCR showing an increase in the expression level of markers of CSC (ALDH1A1, EpCAM, CD133, CD90, CXCR4, NANOG), drug resistance (ABCG2), EMT (CDH12, SNAIL1) and invasion (TGLN) in rs-monolayer.

(FIG. 5A) An invasion assay showing rs-Huh7 cells have higher invasiveness compared to the parental population. (FIG. 5B) Histogram shows the percentage of migration, and (FIG. 5C) the immunoblot and zymogram show an increase in the expression and activity of MMPs, respectively in rs-monolayer population.

(FIG. 7A) Immunofluorescent images showing a marked increase in the expression of ABCG2, a chemoresistant phenotype, in rs-monolayer cells compared to the parental population in multiple cell lines. (FIG. 7B) Difference in the chemosensitivity of parental and rs-monolayer population of Huh7 cells to the antiglycolytic agent 3-BrPA. An increase in $IC_{50}$ of rs-monolayer cells compared to the parental population indicate the requirement of higher concentration of 3-BrPA to achieve similar toxicity. Scale bar represents 20 µm.

FIG. 8A: Tumor initiation by rs-monolayer cells. Equal number of rs-luc-Huh7 or parental luc-Huh7 cells were injected intraperitoneally in to two groups of mice each representing either rs-luc-Huh7 or parental luc-Huh7. Tumor initiation was monitored by BLI as described in Materials and Methods section. As evident by BLI, rs-population formed multiple nodules/lesions compared to the heterogeneous monolayer population. FIG. 8B shows the total flux an indication of total number of viable cancer cells. Rs-Huh7 cells showed higher number of malignant cells compared to the heterogeneous monolayer population. FIG. 8C shows the gross anatomy of mice injected with rs-MCF-7 or MCF-7 (parental cell line). As evident, rs-MCF-7 cells demonstrate massive and aggressive metastatic disease in vivo. The metastasis was compared 3 weeks after intraperitoneal injection of equal number of either parental MCF-7 or rs-MCF-7 cells. FIG. 8D shows that rs-MCF-7 cells have metastatic spread in almost the entire body cavity affecting multiple organs compared to the MCF-7 (parental population) that had lesser aggressive condition. Arrows indicate some of the tumors.

FIG. 11A shows the spontaneous reversal of the human breast cancer cell line, MCF-7 spheroids. Note: Microscopic fillopodia-like or lamellipodia-like structures are prominent in cells at the leading edge (indicated by arrows at the periphery). On Day 3 the migration is at the initial stages whereas on day 5, majority of cells have migrated and spread as evidenced by dense and crowded cell population. FIG. 11B shows human liver cancer cell line, Huh7 spheroids. Huh7 multicellular spheroids aseptically transferred to normal culture condition (adhesive base) resulted in the induction of migration and reversal of spheroid into monolayer. On day 6 majority of the cells migrated from the dense central spheroid-core to the periphery. FIG. 11C shows the leading-edge or periphery of Huh7 spheroid during reversal process. Insert shows overview (low magnification) of the complete spheroid. Scale bar represents 0.5 mm.

DETAILED DESCRIPTION OF THE INVENTION

Figures 1A, 1B, 1C, 1D, 1E, 1F, 1G:
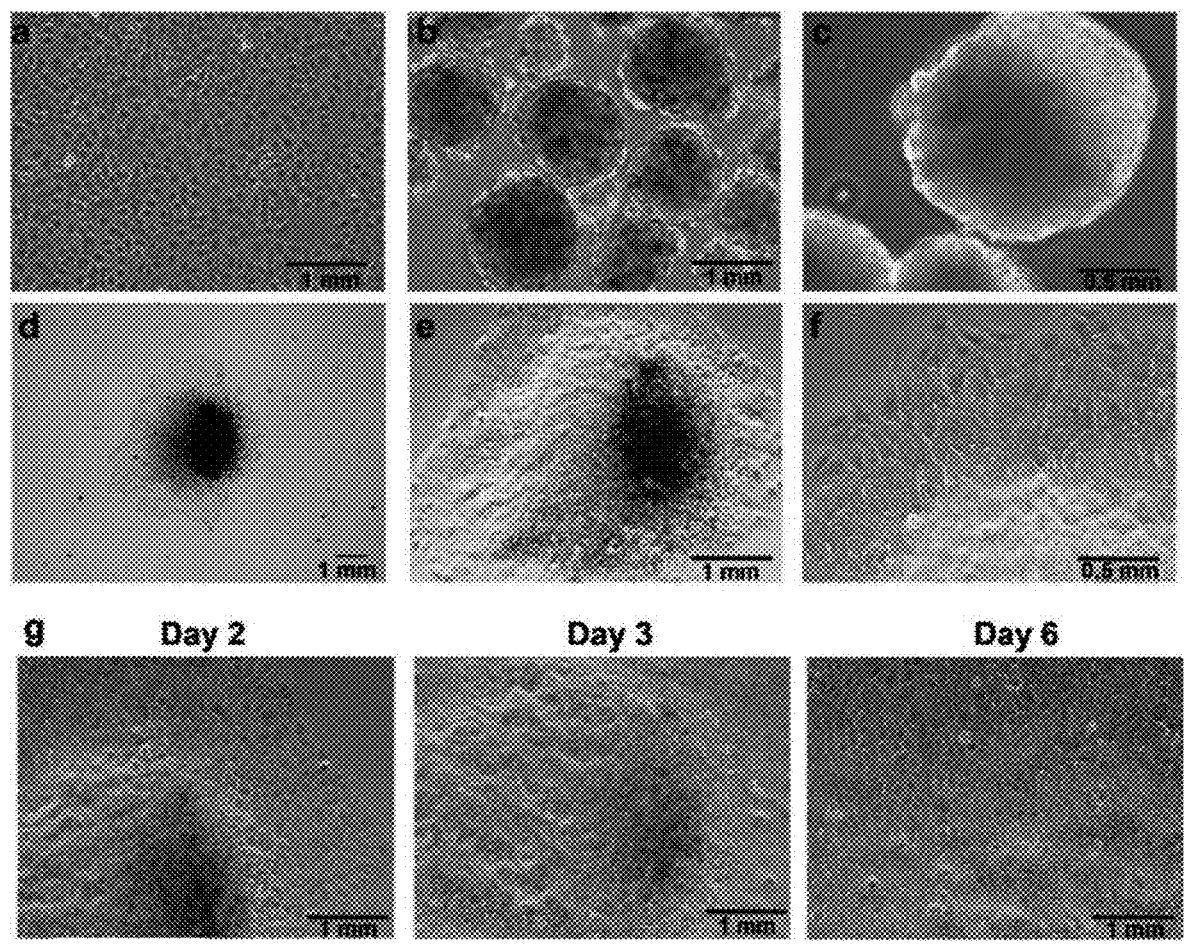
FIG. 1A-1G. Development of anchorage-independent multicellular spheroids and induction of reversal into monolayer.

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

Anticancer agents that show promising results in preclinical investigations rarely succeed in clinics. One of the major challenges that block the success of chemotherapeutics is the resistance rendered by the tumors in patients (chemoresistance). Failure of tumor response to chemotherapy in clinics has been attributed to the presence or emergence of a phenotype that is more aggressive and chemoresistant. In other words, the drug development program initially used to screen and select the prospective anti-cancer agents was based on more sensitive rather than the resistant phenotype seen in the clinics. Hence, it would be highly advantageous if the preclinical evaluation or drug screening could be performed on more aggressive/chemoresistant phenotypes, so as to avoid or reduce the challenges (like resistance) later in the clinics. Until now, there is has been report of any methodology or protocol that describes effective drug screening against chemoresistance or aggressive phenotype. Because cancer cell lines are heterogeneous in their population, drug screening against chemoresistant phenotype is understandably complicated. However, a few researchers have explored the possibility of creating "near-in vivo" models such as three-dimensional cell cultures which are different from conventional monolayer (two-dimensional) cultures. These three-dimensional cultures are referred as spheroids or multicellular spheroids (MCS). However, the generation of spheroids was obtained either through the addition of gel-like substances or chemical chelating agents (such as EDTA, linkers) and the like. See FIG. 1. This additional experimental manipulation is certainly bound to affect the cellular property at biochemical as well as physiological levels. Moreover, the penetration of putative anti-cancer compounds to the inner core or center of the spheroids is uncertain as it depends on the nature of the compound (whether they can be quenched by outer layer of cells), as well as the size of the spheroids (larger the size the lesser the penetration efficiency). Hence, it is difficult to interpret whether any chemoresistance observed in such spheroids is due to the innate property of cellular-resistance or its physical barrier (three-dimensional architecture) against drug penetration. See Friedrich et al., 4 NAT. PROTOC. 309-24 (2009); Desoize, B., 36 CRIT. REV. ONCOL. HEMATOL. 59-60 (2000); Desoize, B. and Jardillier, J., 36 CRIT. REV. ONCOL. HEMATOL. 193-207 (2000). Intriguingly, a recent report demonstrated that human cancer cells in 3D-culture are more sensitive to doxorubicin (a clinically used anticancer drug) than its corresponding monolayer culture [Gomes L R, Vessoni A T, Menck C F. Three-dimensional microenvironment confers enhanced sensitivity to doxorubicin by reducing p53-dependent induction of autophagy. Oncogene. 2015 Jan. 26. doi: 10.1038/onc.2014.461. [Epub ahead of print]

PubMed PMID: 25619836]. This reveals that under experimental conditions the microenvironment of 3D culture could make cancer cells more sensitive than expected resistance. This could eventually mislead the identification of a fallacious compound as potential anticancer agent that may be less-effective under clinical conditions. Here, an in vitro method was designed with a few modifications of conventional in vitro assays. Huh7 cells, a human hepatocellular carcinoma (HCC) cell line which has been known to exhibit diverse sensitivity to several anticancer agents, were used as a model. See Hoshida et al., 54 HEPATOGASTROENTEROLOGY 489-92 (2007); and Muller et al., 99(3) J. CLIN. INVEST. 403-13 (1997).

Essentially, using ultra-low attachment culture conditions, a population of Huh7 cells was isolated exhibiting anchorage-independent phenotype. These anchorage-independent cells formed reversible spheroids (spherical, ball like structures due to the aggregation of cells), i.e., transformation of spheroids into monolayer or vice versa depending upon the adhesive (attachment)/non-adhesive (ultra-low attachment) culture conditions. See FIG. 2. These reversible spheroids demonstrated several properties of a typical aggressive phenotype, e.g., migration or invasion (metastatic potential), self-renewal and proliferation even in an unfavorable condition such as absence of adhesion (cancer stem-like property). Notably, these cells exhibited differential chemosensitivity to a panel of anticancer agents compared to their parental monolayer cells. These reversible spheroid cells were found to be resistant to a majority of the anticancer agents. Interestingly, they were more sensitive to some of the anticancer agents than their parental monolayer cells. The majority of anti-cancer agents that were effective against the parental monolayer Huh7 cells were resisted by this subpopulation of anchorage-independent cells. This indicates that screening against such anchorage-independent population would have indicated a different class of anticancer agents as potent inhibitor of Huh7 cells or HCC cells.

Thus, in certain embodiments, anticancer agent screening can be performed against both the reversible spheroid cells (aggressive phenotype) and the parental monolayer cells in order to identify a potent or effective anticancer agent(s), or at least a combination of agents to achieve antitumor effects overcoming tumor-heterogeneity mediated resistance.

In certain embodiments, non-adhesive culture conditions can be accomplished using commercially available low/ultra-low attachment plates, flasks, etc. See Ultra-Low Attachment products from Corning Incorporated (Corning, N.Y.) (e.g., products nos. 3477, 7007, and 3827); and Nanoculture® plates from Scivax USA, Inc. (Woburn, Mass.). In such embodiments, the surface of the plate/flask prevents attachment of normally anchorage-dependent cells. Anchorage-independent cells, such as tumor cells, will grow as stationary suspension cultures when cultured on the surface, often forming unattached spheroids.

These growth vessels have a very hydrophilic and neutrally charged hydrogel layer that is covalently linked directly to the polystyerene surface to prevent peeling. Although not wishing to be bound by any particularly theory, because cell attachment proteins and other biomolecules passively adsorb to polystyrene surfaces through either hydrophobic or ionic interactions, this hydrogel surface naturally inhibits non-specific immobilization via these forces, thus inhibiting subsequent cell attachment. The vessel surface is very stable, non-cytotoxic and biologically insert.

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Example 1

Reversal of Anchorage-Independent Multicellular Spheroid into a Monolayer Mimics a Metastatic Model Lack of an in vitro model of metastasis has been a major impediment in understanding its biology and identification of potential therapeutic targets. We have developed a metastatic model by the induction of reversal of anchorage-independent multicellular spheroid into a monolayer which displayed the signatures of metastatic phenotype (migration, invasiveness, and chemoresistance besides the expression of cancer stem-cell markers). Besides delineating the molecular events of metastasis, this model could also improve the screening efficiency of antimetastatic agents.

In particular embodiments, the present invention provides for the isolation and enrichment of cancer cells with clonogenic (malignant) phenotype based on anchorage-independence for further development into metastatic model. These cancer cells were in multicellular spheroid form. In addition, the generation of multicelullar spheroids does not involve any chemical addition (gel, linkers, EDTA, etc.) or manipulation (constant shaking in rotator shaker), avoiding their interference in cell physiology.

As described herein, the multicellular spheroids were transferred to normal (anchorage-dependent) culture system to induce migration and dispersion of cells from spheroids into monolayer. Surprisingly, this monolayer, known as reversed-spheroid monolayer, retained the phenotypic characteristics of cancer stem cells and epithelial mesenchymal transition (EMT). Noteworthy, these are usually typical properties of anchorage-independent or clonogenic states and not monolayer cells. Thus, a spontaneous reversal of anchorage-independent multicellular spheroids resulted in a monolayer with migratory, invasive, resistant and cancer-stemlike model mimicking an in vitro model of metastasis.

Materials and Methods

Cell Culture, Chemical and Reagents.

Human hepatocellularcarcinoma (HCC) cell lines HepG2, Hep3B and SK-Hep1 were obtained from the American Type Culture Collection (ATCC) (Manassas, Va., USA). Huh7 cells were kindly provided by Dr. James Hamilton of the Gastroenterology & Hepatology department. The MCF-7 cells were obtained from ATCC (USA). The HCC cell lines SK-Hep1, HepG2, Hep3B were maintained in modified Eagle's medium (Life Technologies Inc., Grand Island, N.Y., USA) supplemented with 10% fetal bovine serum (FBS) (Thermo Scientific Hyclone Inc., Waltham, Mass., USA), and 1% antibiotics, penicillin and streptomycin, sodium bicarbonate and sodium pyruvate (Gibco, Carlsbad, Calif., USA). Huh7 cells were cultured in RPMI medium (Life technologies) with 10% FBS and 1% antibiotics. MCF-7 cells were cultured in modified Eagle's medium (Life Technologies) supplemented with 0.01 mg/ml bovine insulin, in addition to 10% FBs and 1% antibiotics.

Anchorage-Independent Growth and Induction of Reversal of Multicellular Spheroids (MCSs).

To generate MCS from a heterogeneous parental population cells growing log phase were seed in ultra-low attachment 6-well plates (Corning Inc. PA, USA) and cultured in complete growth medium at 37° C. and 5% $CO_2$. No gel matrix or matrigel-like materials were used. Cells that survived this anchorage-independent condition aggregated and formed spheroids whereas cells that could not survive this selection pressure died and were floating loose independent bodies. The spheroids generated in such ultra-low attachment culture conditions were separated from dead or unhealthy (based on the cellular morphology) cells and cultured further. To induce reversal of spheroid cells, the MCS was aseptically transferred to regular culture dish that supports adhesion of epithelial cells. Cells were allowed to migrate from spheroid into surface of the dish and media was changed as may be necessary. Once the spheroid has completely reversed to monolayer the cells were trypsinized and propagated as per regular cell culture conditions.

Generation of Luc-Huh7 Cells for Phenotypic Microarray (PMM) Analysis.

For PMM array studies, the luciferase reporter plasmid pcDNA 3.1-cytomegalovirus-firefly luciferase was provided by Martin Pomper that was initially generated in Sam Gambhir's laboratory as described. Huh7 cells stably expressing luciferase gene were generated by transfecting them with pcDNA 3.1-cytomegalovirus-firefly luciferase plasmid by using a transfection agent (TurboFectin 8.0; OriGene Technologies), followed by clonal selection with G418 (Invitrogen, Grand Island, N.Y.) containing growth medium. Clones expressing highest luciferase activity were selected and used for further studies. For simplicity, these stable cells will be referred hereafter as luc-Huh7.

qRT-PCR.

Gene expression analysis was performed by using quantitative real-time polymerase chain reaction with a sequence detection system (ABI 7900HT; Applied Biosystems, Bedford, Mass., USA) and a mix (SYBR Green PCR Master Mix; Applied Biosystems). In brief, total RNA was extracted and cDNA was synthesized as described previously. The complementary DNAs thus synthesized were subjected to quantitative real-time polymerase chain reaction for specific gene expression analysis. The primers used for respective gene amplification were synthesized by RealTimePrimers.com (Elkins Park, Pa., USA).

The primers used were as follows: 5'-TTGTTCCTGGT-TATGGGCCT-3' (forward) (SEQ ID NO:1) and 5'-TCCAGTTTGGCCCCTTCTTT-3' (reverse) (SEQ ID NO:2) for ALDH1A1; 5'-TAAAAGTTTGCGGACTGCAC-3' (forward) (SEQ ID NO:3) and 5'-GCCACATCAGC-TATGTCCAC-3' (reverse) (SEQ ID NO:4) for EPCAM; 5'-CCTCTGGTGGGGTATTTCTT-3' (forward) (SEQ ID NO:5) and 5'-CAGTTTCCGACTCCTTTTGA-3' (reverse) (SEQ ID NO:6) for PROM1; 5'-AGGAAGCCT-CAAGTTCCAGT-3' (forward) (SEQ ID NO:7) and 5'-AAAAGACAGCCAGAGGTGTG-3' (reverse) (SEQ ID NO:8) for THY1; 5'-GGTGGTCTATGTTGGCGTCT-3' (forward) (SEQ ID NO:9) and 5'-TG-GAGTGTGACAGCTTGGAG-3' (reverse) (SEQ ID NO:10) for CXCR4; 5'-ACCTACCTACCCCAGCCTTT-3' (forward) (SEQ ID NO:11) and 5'-CATGCAGGACTGCAGAGATT-3' (reverse) (SEQ ID NO:12) for NANOG; 5'-TAAAGTGGCAGACTCCAAGG-3' (forward) (SEQ ID NO:13) and 5'-TTGTTCGTCCCTGCTTAGAC-3'(reverse) (SEQ ID NO:14) for ABCG2; 5'-TGGATGGACCTTATGTTGCT-3' (forward) (SEQ ID NO:15) and 5'-AACACCTGTCTTGG-GATCAA-3' (reverse) (SEQ ID NO:16) for CDH12; 5'-ACCCCACATCCTTCTCACTG-3' (forward) (SEQ ID NO:17) and 5'-TACAAAAACCCACGCAGACA-3' (reverse) (SEQ ID NO:18) for SNAI1; and 5'-GCAGTC-CAAAATCGAGAAGA-3' (forward) (SEQ ID NO:19) and 5'-ACCAGCTTGCTCAGAATCAC-3' (reverse) (SEQ ID NO:20) for TAGLN. The internal control primer set 18S was used (Applied Biosystems).

Figure 14:
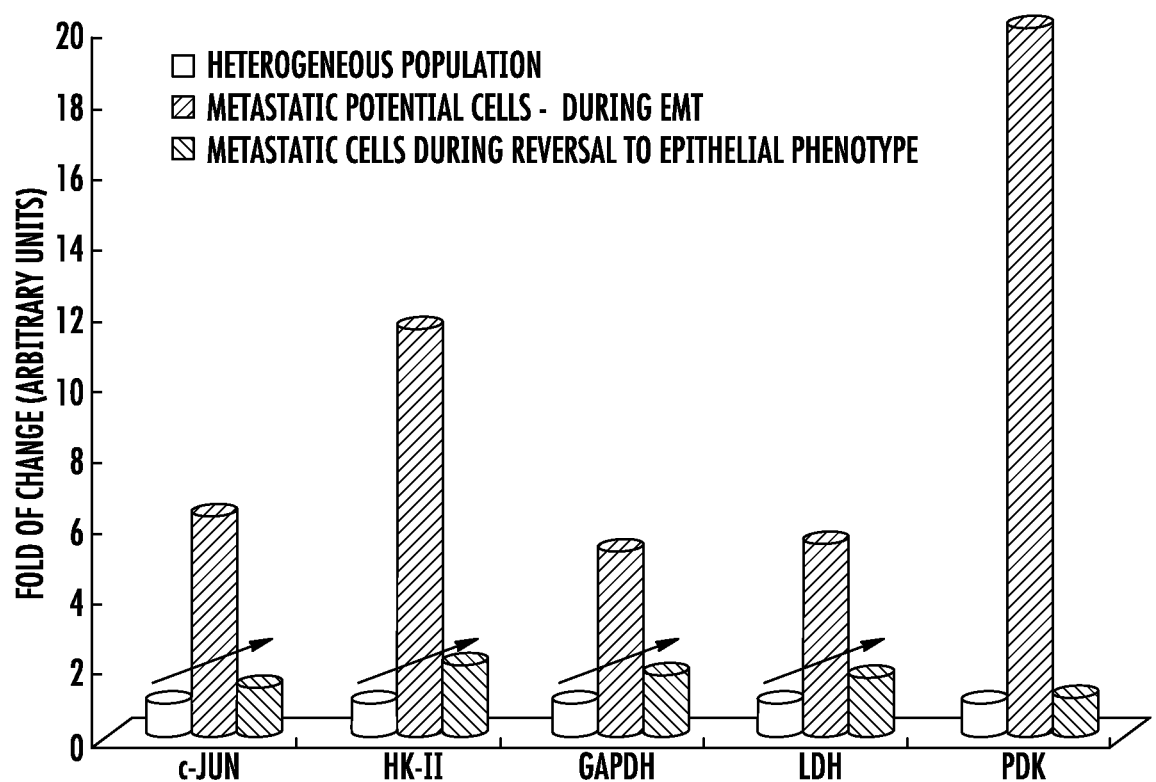
FIG. 14. Metabolic reprogramming (one of the hallmarks of cancer) achieved during EMT (induction of spheroids) results in an increase in the metabolic capacity of reversed spheroid monolayer. qRT-PCR was performed as described in the Materials and Method section using gene specific primers. HK-II—hexokinase II, GAPDH—glyceraldehyde-3-phospate dehydrogenase, LDH—lactate dehydrogenase and PDK—pyruvate dehydrogenase kinase.

The primers used for the data shown in FIG. 14 were as follows:

```
(forward)
                                          (SEQ ID NO: 21)
5'-GAGTCAACGGATTTGGTCGT-3'
and (reverse)
                                          (SEQ ID NO: 22)
5'-TTGATTTTGGAGGGATCTCG-3' for GAPDH;

(forward)
                                          (SEQ ID NO: 23)
5'-TCCCCTAACCTCTTTTCTGC-3'
and (reverse)
                                          (SEQ ID NO: 24)
5'-AACATCGCACTATCCTTTGG-3' for c-jun;

(forward)
                                          (SEQ ID NO: 25)
5'-ATACGGATCAGAAACCGACA-3'
and (reverse)
                                          (SEQ ID NO: 26)
5'-CAGACGCCTAGCATTTTCAT-3' for PDK;

(forward)
                                          (SEQ ID NO: 27)
5'-TGCCAAGCGTCTACATAAGA-3'
and (reverse)
                                          (SEQ ID NO: 28)
5'-GCTCCATTTCTACCTTCATCC-3' for HKII;
and (forward)
                                          (SEQ ID NO: 29)
5'-AGGCTACACATCCTGGGCTA-3'

(reverse)
                                          (SEQ ID NO: 30)
and
5'-CCCAAAATGCAAGGAACACT-3' for LDH.
```

Invasion Assay.

Invasion assay was performed using the CytoSelect Invasion assay kit from Cell Biolabs Inc. (San Diego, Calif., USA). The assay was performed as per manufacturer's instructions and at the end of 24 hours of invasion, cells were stained and microscopic images were captured prior to the colorimetric quantification.

Gelatin Zymography for Matrix Metalloproteinase (MMP) Activity.

The level of MMP activity in the conditioned medium of parental cell lines as well as rs-monolayer population was quantified by gelatin zymography. Protein (7.5 μg) samples from the conditioned media of respective cell lines were subjected to zymography using 10% gelatin-zymogram gel (Invitrogen, CA). The staining procedures were followed as per the supplier's instructions. In brief, at the end of electrophoresis, the gel was incubated in zymogram renaturation buffer for 30 minutes at room temperature, followed by an overnight incubation with the zymogram developing buffer at 37° C. or room temperature. Next, the gel was stained with colloidal coomassie blue followed by destaining. The MMP activity was visualized as clear bands.

Immunostaining and Immunoblotting.

Phenotypic analysis of metastatic markers was performed using immunodetection of specific targets followed by the acquisition of images in a confocal microscopy. In brief, the cells were grown in Lab-Tek II chamber slides (Thermo Fisher Scientific Inc. PA, USA) containing appropriate growth medium. They were fixed with 4% formaldehyde for 10 minutes, rapidly rehydrated with phosphate-buffered saline (PBS) and permeabilized with 0.5% Triton X-100 solution in PBS.

Immunostaining protocols were followed as per antibody suppliers' instructions, and the DAPI (Invitrogen, CA) nuclear stain was used as the counter-stain. In methods where non-conjugated primary antibodies were used corresponding secondary antibodies with either FITC (anti mouse, Sigma Inc., USA) or PE conjugate (anti-rabbit, Cell Signaling Technology, Boston, Mass., USA) were used as per suppliers' instructions. Transgelin was stained with mouse monoclonal antibody (Santa Cruz Biotechnology Inc., CA), vimentin was stained with Alexa Fluor conjugated rabbit monoclonal antibody (Cell signaling Technology Inc.), CXCR4 was stained with mouse monoclonal antibody (Santa Cruz Biotechnology Inc.) EpCAM was stained with Alexa Fluor conjugated mouse monoclonal antibody (Cell Signaling Technology Inc.) and CD 133 was stained with rabbit monoclonal antibody (Cell Signaling Technology Inc.) and ABCG2 was stained with mouse monoclonal antibody (Santa Cruz Technology Inc.). The slides were mounted with ProLong Gold anti-fade mounting media (Invitrogen) before microscopic analysis. Images were Fluorescent images of immunostained slides were acquired with Zeiss 510 Meta LSM Confocal Microscope at the Microscope facility, Johns Hopkins School of Medicine. The size of images was adjusted across all pictures using Adobe Photoshop software for better clarity in the final figures.

Immunoblotting of MMP-2 was performed using rabbit monoclonal antibody (Cell Signaling Technology Inc.). In brief, ~7 ug of samples from the conditioned media of various cells lines were electrophoretically resolved on 4-12% Bis-Tris gel (Invitrogen) with MOP-SDS buffer and blotted onto PVDF membranes (Bio-Rad) and blocking and detection were performed as described before but using the specific MMP-2 antibody. Immune complexes were visualized by ECL-detection kit (GE Health Care).

Chemosensitivity Assay.

Assessment of the chemosensitivity of parental cell population and rs-monolayer population was performed using the antiglycolytic agent, 3-bromopyruvate (3-BrPA). In brief, cells were plated in 96-well plates the day before treatment. Analysis of cell viability following the addition of 3-BrPA was performed as described other cell lines[22].

Animal Experiments.

Animal studies were performed as approved by the Johns Hopkins University Animal Care and Use Committee. For the in vivo experiments, 4-5-week-old male athymic nude mice (body weight, 25-30 g) were used (Crl:NU-Foxn1nu strain; Charles River Laboratory, Germantown, Md.). Tumor initiation investigated by intraperitoneal injection of either heterogeneous population or rs-population of luc-Huh7 cells ($5 \times 10^6$ cells/mouse). Tumor initiation or growth was monitored by bioluminescence imaging.

Phenotypic Microarray (PMM) Analysis.

Luc-Huh7 cells of parental population or rs-monolayer were used for the PMM array analysis. In brief, 96-well plates, pre-coated with anticancer agents at four-different increasing concentrations (1×, 2×, 3× and 4×) were used to test the chemosensitivity of these two phenotypes (monolayer and reversed-spheroids). After a period of 36 hours of incubation in PMM plates the chemosensitivity of parental and rs-monolayer population was assessed based on the bioluminescence signal generated by luciferase which is an indicator of intracellular ATP level and cell viability.

Results

Figures 9A, 9B, 9C, 9D, 9E, 9F:
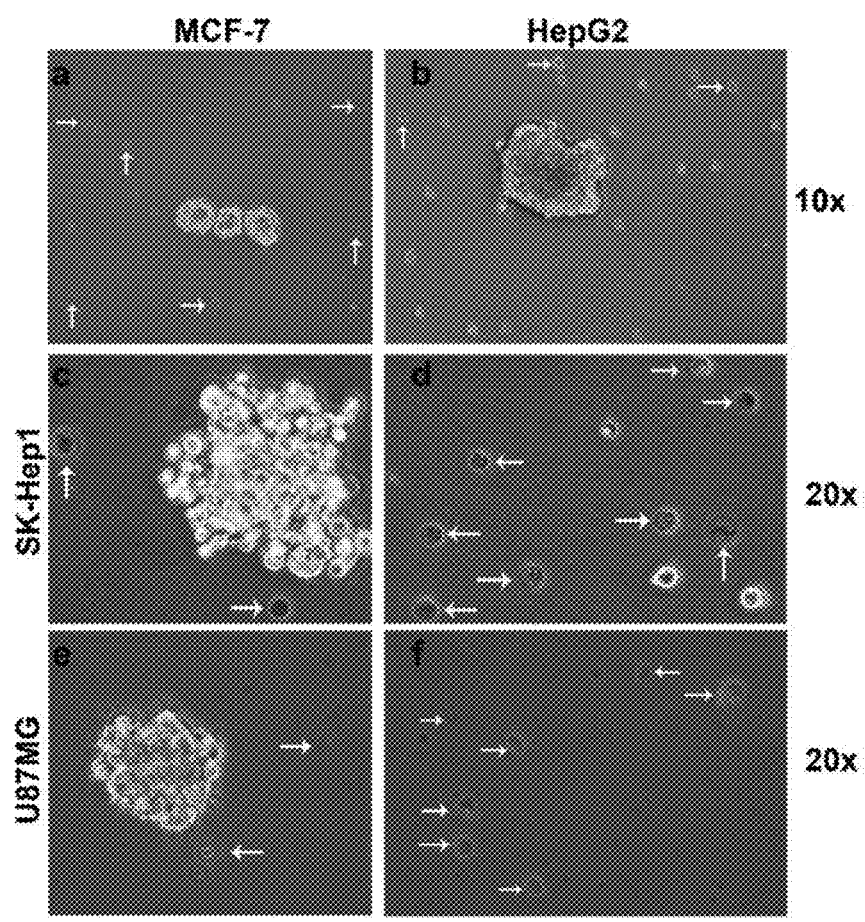
FIG. 9A-9F. Development of multicellular aggregates or spheroids by anchorage-independence. Culture of cancer cell lines under ultra-low attachment condition generated multicellular aggregates or spheroids. Arrows indicate cells that did not survive the selection by ultra-low attachment. The three cell lines which represent breast (MCF-7), liver (SK-Hep1) and brain (U87MG) cancers substantiate that the selection strategy is relevant/applicable to several types of solid malignancies.

MCS generated without the use of exogenous gel-like materials (e.g., matrigel) spontaneously reversed into monolayer under normal culture condition. The reversal process involved migration of cells from the spheroidal structure towards the base of the MCS. FIG. 1 (upper panel) shows a schematic representation of the conventional monolayer cells with tumorigenic population, followed by the recent advancement over the monolayer culture resulting in 3D MCS, and the proposed model of induction of reversal of spheroids. We subjected parental populations of cells (FIG. 1A) to ultra-low attachment culture conditions necessitating an anchorage-independent growth to form MCS (FIG. 1b-c). One of the advantages of MCS that are grown under anchorage-independence is the selection of clonogenic- or aggressive-phenotypic cells. The proliferative but non-malignant cells that often dominate any heterogeneous parental cell line will be eliminated due to the loss of viability (FIG. 9).

Figure 10:
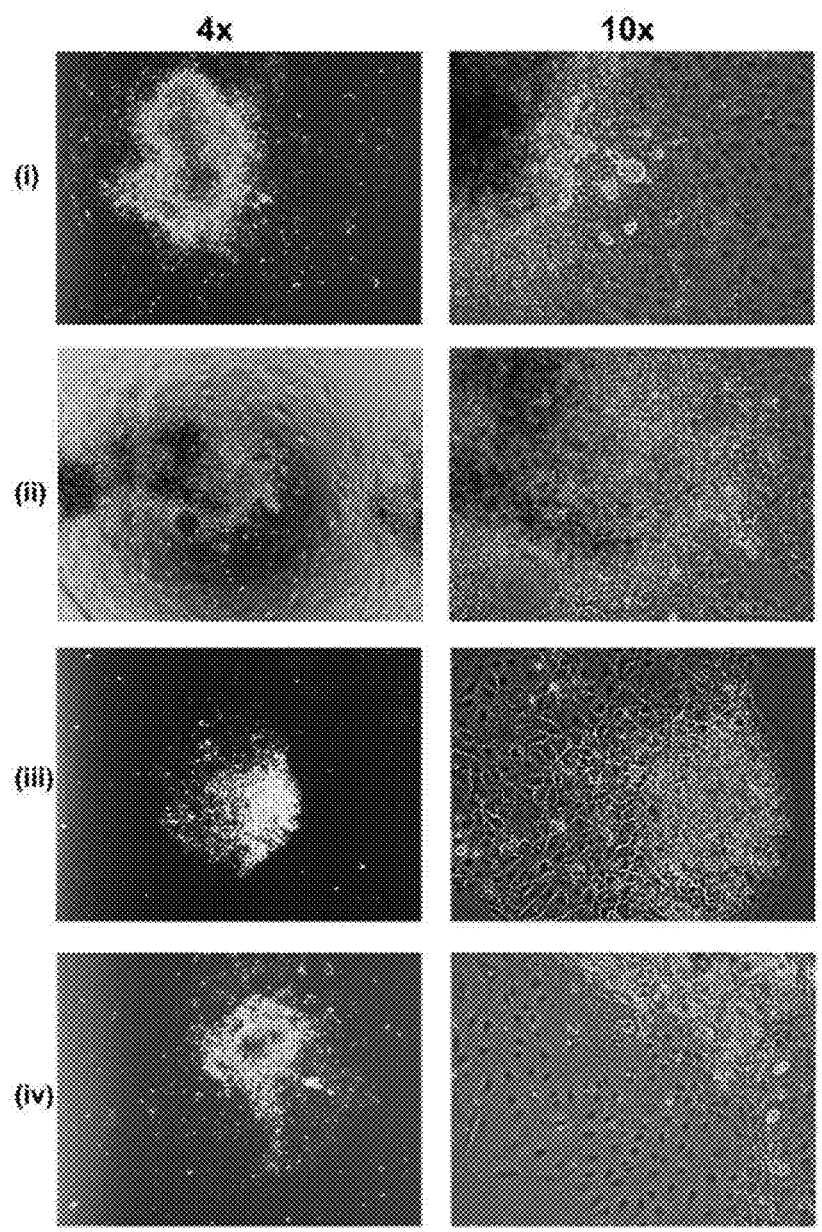
FIG. 10. Induction of reversal of multicellular spheroid into monolayer. Multicellular spheroids aseptically transferred to normal culture condition (adhesive base) resulted in the induction of migration and reversal of spheroid into monolayer. Images are the representation of Huh7 cells.
Figures 11A, 11B, 11C:
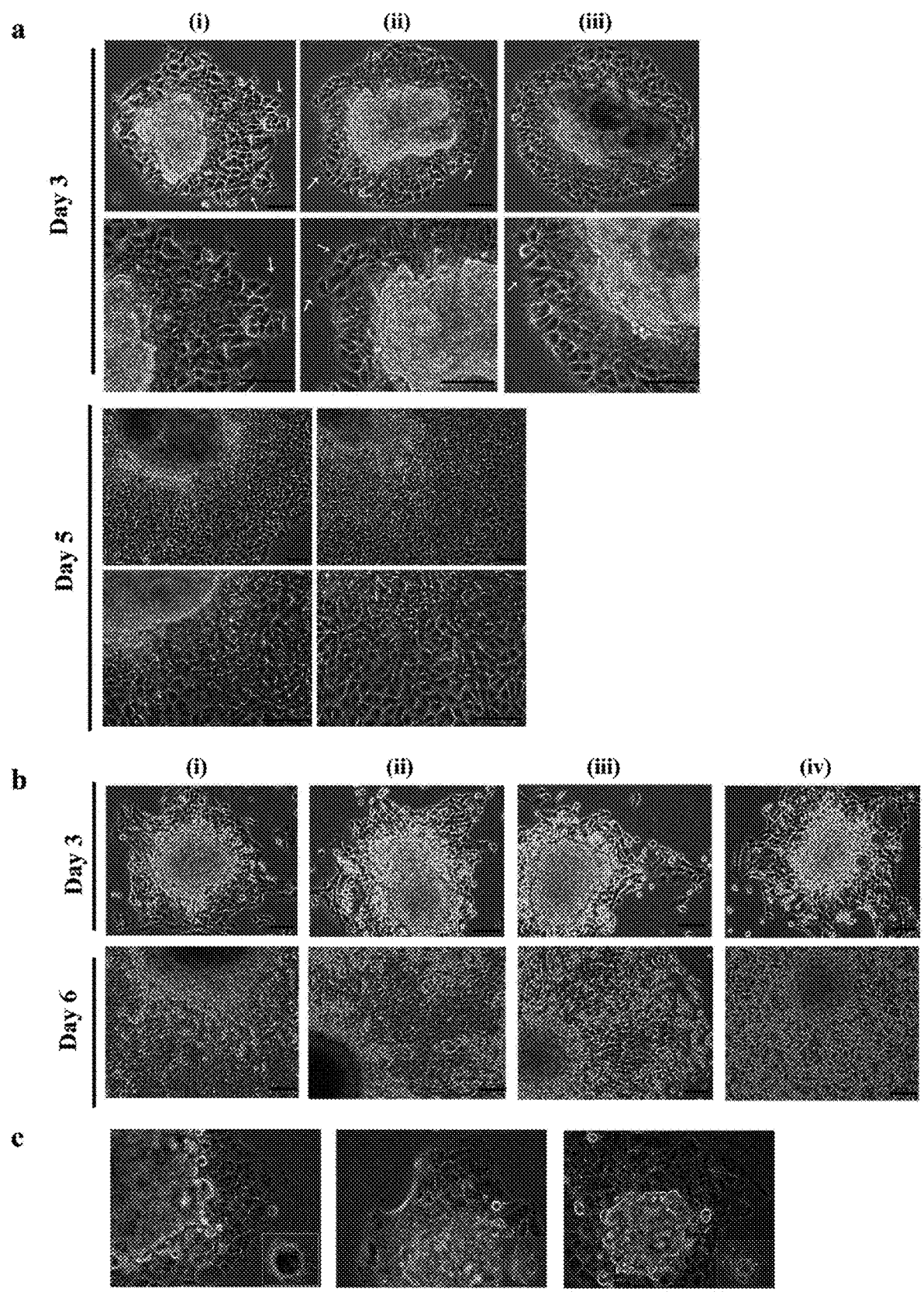
FIG. 11A-11C. Spontaneous reversal of malignant cells. The reversal of spheroid followed a consistent pattern with the migration of cells at the periphery followed by cells from the middle or central region.

Following the generation of MCSs by anchorage-independence, we next induced the reversal of spheroids (for simplicity here after referred as rs) by transferring them into normal (adhesive) culture condition (FIG. 1d-f). During the reversal process, cells were observed to migrate in a "downhill" fashion from the vertical top axis of the spheroid to its base which is close to the attachment/adhesive-surface, but in a direction away from the spheroid-base (FIG. 1g). These events were consistent and verified in multiple cancer cell lines (FIG. 10). The complete downward migration of cells from the vertical axis (top) to form the rs-monolayer (by reversal) required ~7 days and it primarily depended upon the size of the spheroid and type of cancer cells. Interestingly, during the process of migration, cells exhibited typical features of motility such as fillopodia or pseudopodia like protrusions prior to migration (FIG. 11).

Figure 2A:
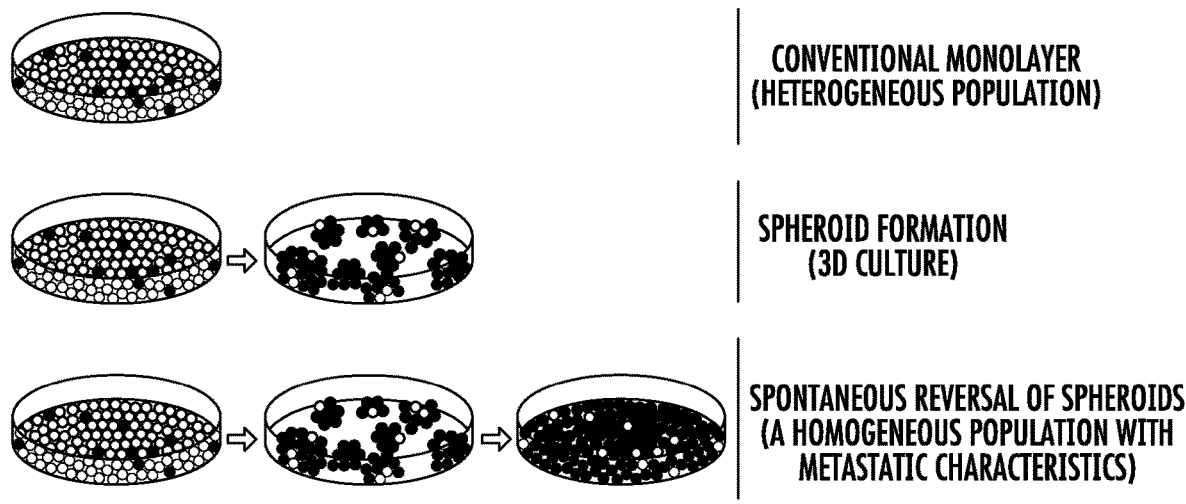
FIG. 2A-2B.
Figure 2B:
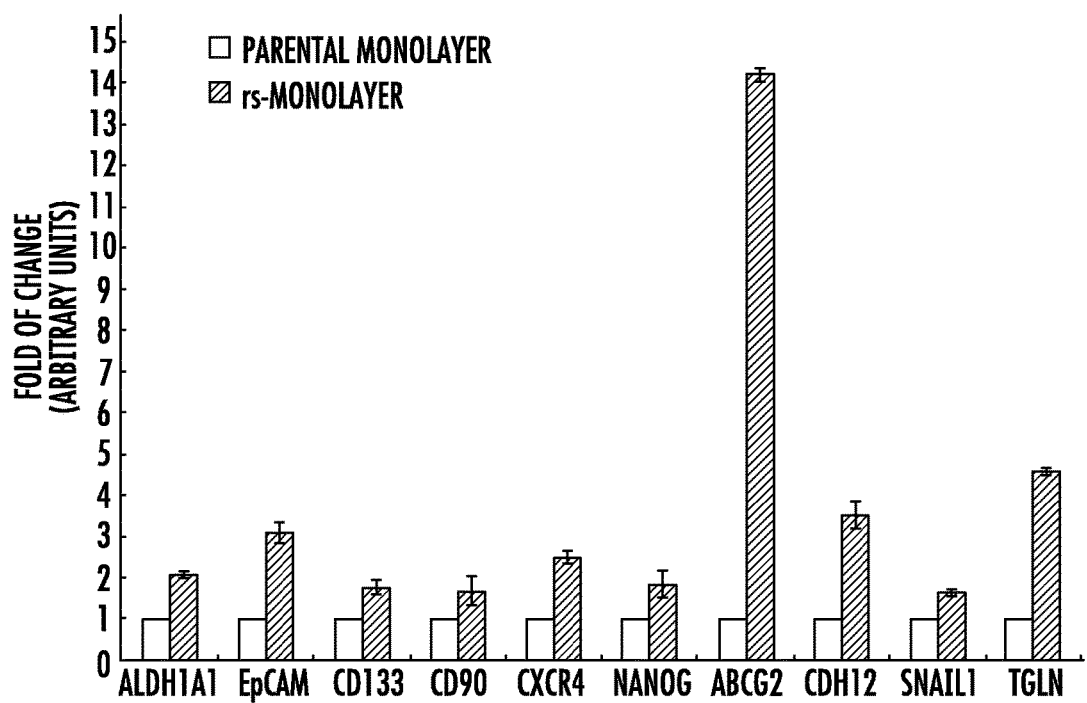
Figure 3:
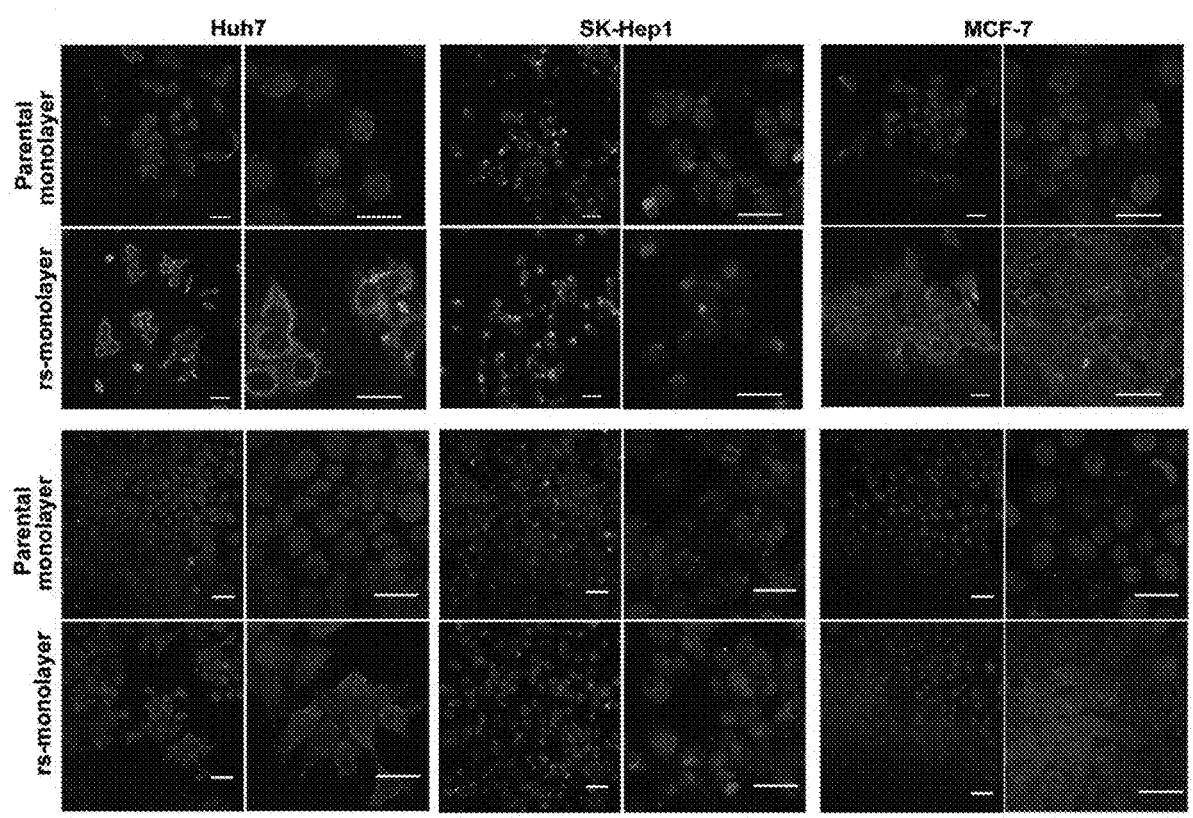
FIG. 3. Overexpression of transgelin in rs-monolayer population. Immunofluorescent images showing a marked increase in the expression of transgelin in the rs-monolayer compared to the parental population in multiple cell lines. Scale bar represents 20 µm.
Figure 4:
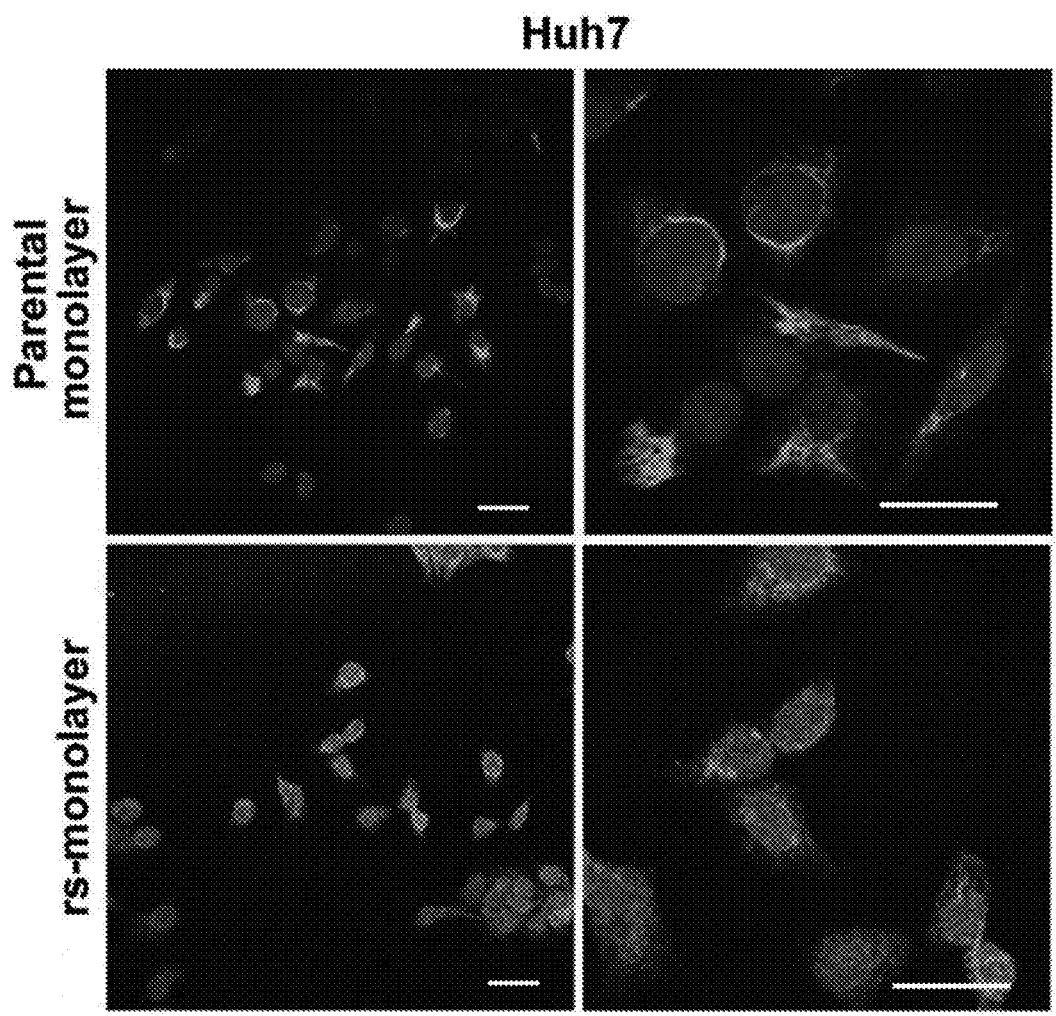
FIG. 4. Overexpression of vimentin in rs-monolayer population. Immunofluorescent images showing a marked increase in the expression of vimentin, an EMT marker, in the rs-monolayer compared to the parental population of Huh7 cells. Scale bar represents 20 µm.

Next, we evaluated if this reversal in morphology correlated with metastatic genotype. Data from quantitative RT-PCR (qPCR) analysis showed a marked increase in the expression of cancer-stem cell (CSC) markers (ALDH1A1, EpCAM, CD133, CD90, CXCR4, NANOG), as well as genes associated with drug resistance (ABCG2) and invasiveness (TGLN, Snail1, CDH12) in rs-monolayer cells (FIG. 2). We then verified if the elevation in the mRNA level of genes associated with metastasis or invasion correlated with the phenotypic expression of corresponding proteins in rs-monolayer. Immunofluorescent analysis of transgelin, a protein associated with migration, showed a marked increase in its expression in the rs-monolayer of multiple cell lines such as Huh7, SK-Hep1 and MCF-7 indicating the enrichment of metastatic cells in rs-population (FIG. 3). Similarly, the expression of the EMT marker, vimentin, is increased in rs-monolayer despite being reversed to epithelial-monolayer phenotype thus demonstrating that the markers of EMT are retained in the rs-monolayer population (FIG. 4). Together, the mRNA expression level as well as the phenotypic expression of corresponding proteins indicate that the rs-monolayer population is highly metastatic than the parental population.

Figures 5A, 5B, 5C:
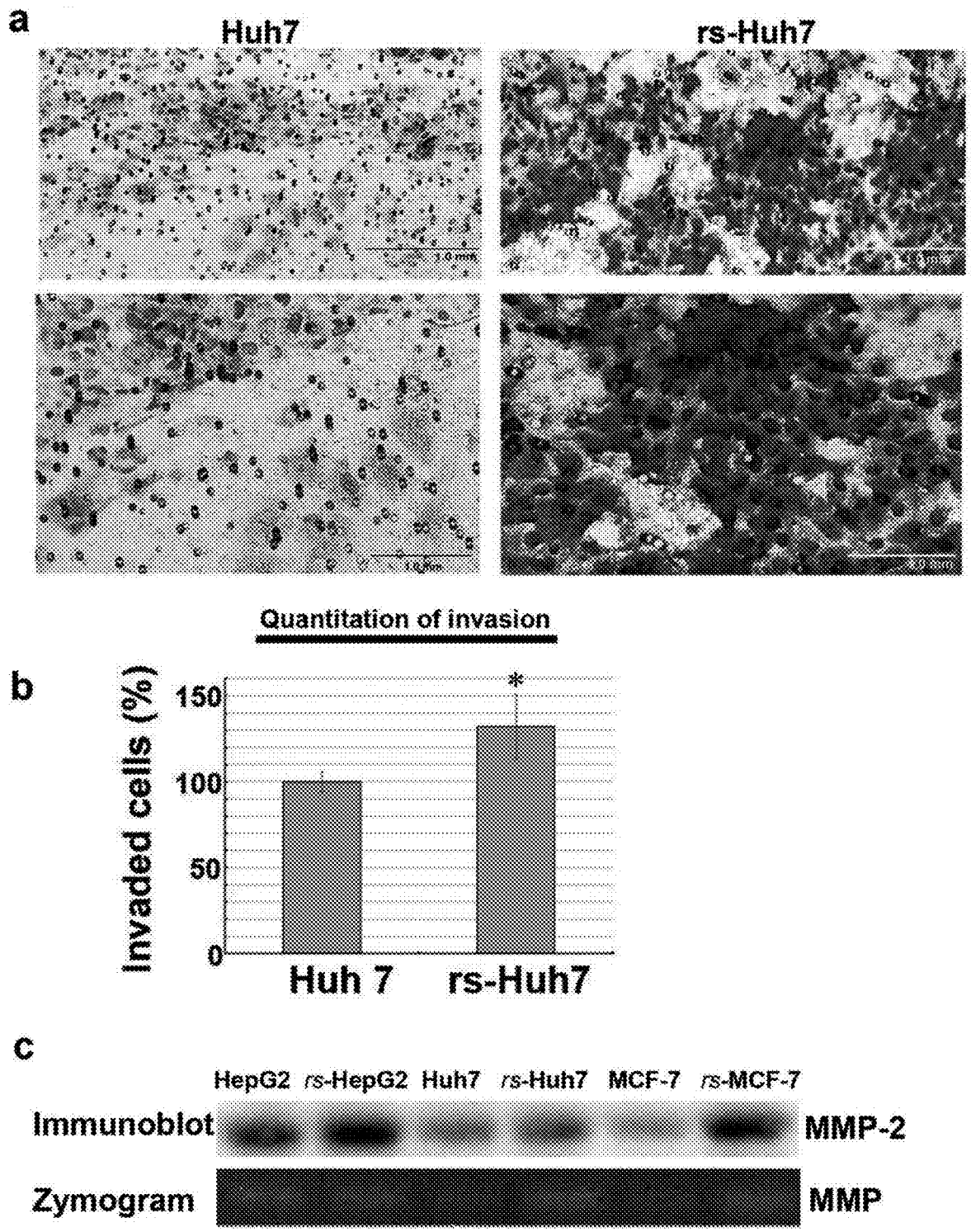
FIG. 5A-5C. rs-monolayer cells are highly invasive than the parental population.
Figure 6:
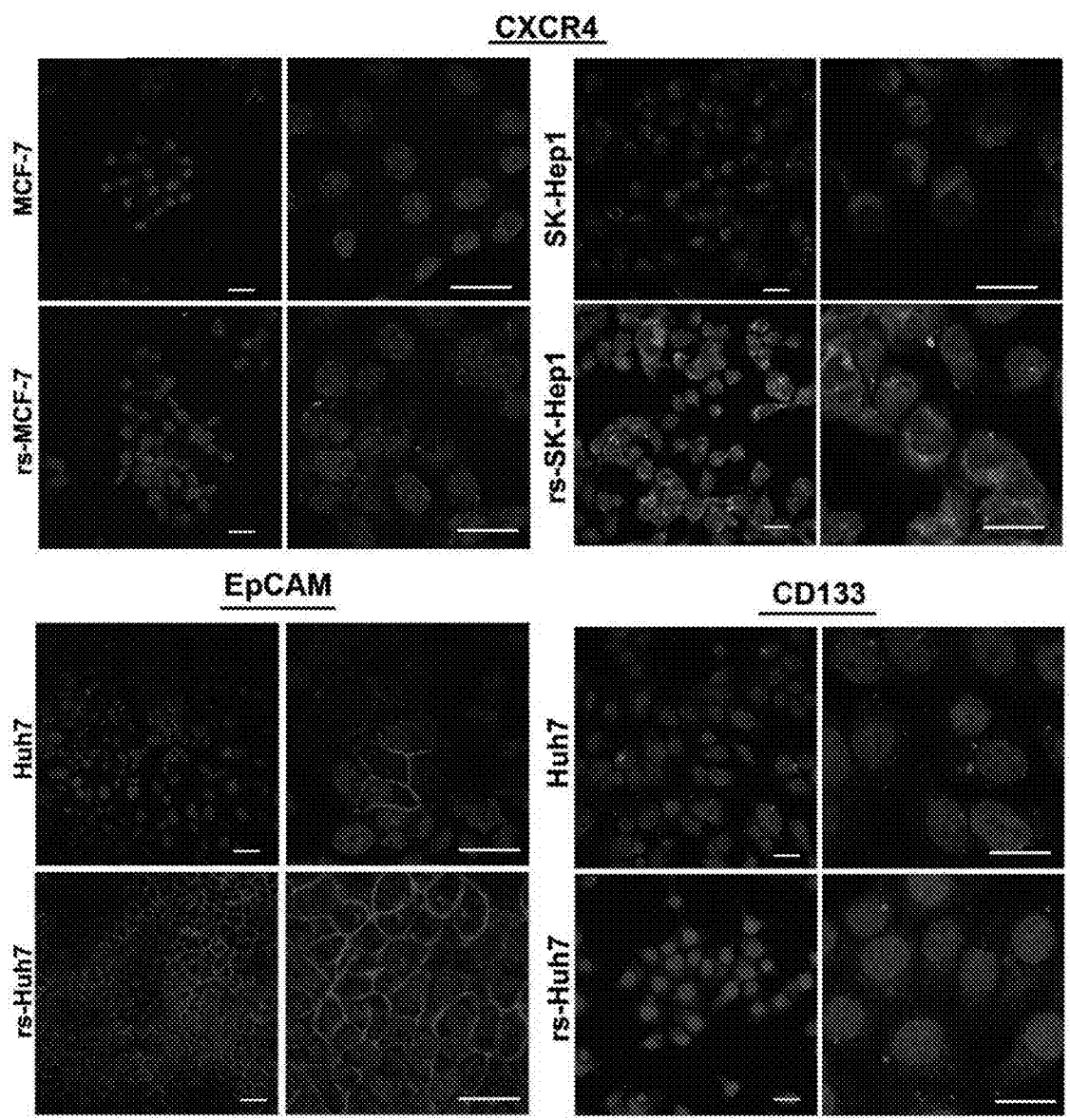
FIG. 6. Overexpression of cancer-stem cell markers in rs-monolayer population. Immunofluorescent images showing a marked increase in the expression of CSC markers such as CXCR4, EpCAM and CD133 in rs-monolayer cells compared to the parental population. Scale bar represents 20 µm.
Figure 12:
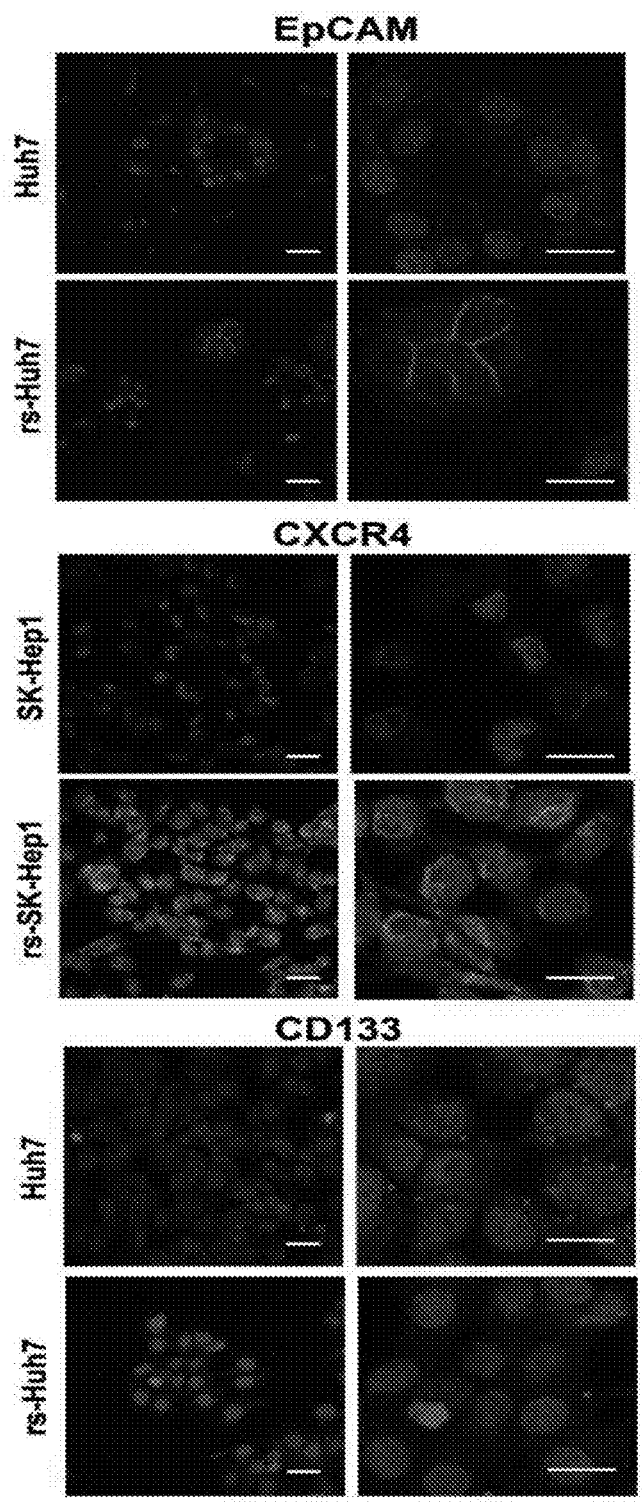
FIG. 12. Cancer stem cell markers are upregulated in the rs-monolayer. Multiple cancer cell lines demonstrate that cancer stem cell markers such as EpCAM, CXCR4 and CD133 expression are increased in rs-monolayer cells compared to the parental cell line. Scale-bar represents 20 µM.

Functional analysis revealed that the invasive capacity of rs-monolayer markedly high compared to the parental population. Data from the invasion assay demonstrated that the rs-monolayer has higher number of invading cells than the parental cell line indicating the enrichment of metastatic population in rs-monolayer (FIG. 5a,b). Analysis of matrix metallo proteases (MMP) activity by zymogram and its expression by immunoblot showed increased activity and an elevation in the level of expression (FIG. 5c). This corroborated the higher invasive-ability of rs-monolayer cells compared to the parental population. Thus, rs-monolayer exemplifies migratory and invasive characteristics that are integral components of metastatic processes. Further, the aggressive metastatic phenotype was also complemented by the expression level of cancer-stem cell (CSC) markers such as CXCR4, EpCAM and CD133. Immunofluorescent analysis showed that the rs-monolayer population exhibit higher expression level of CSC markers compared to their corresponding parental population indicating the enrichment of CSC-like cells in the rs-monolayer (FIG. 6, FIG. 12).

Figures 7A, 7B:
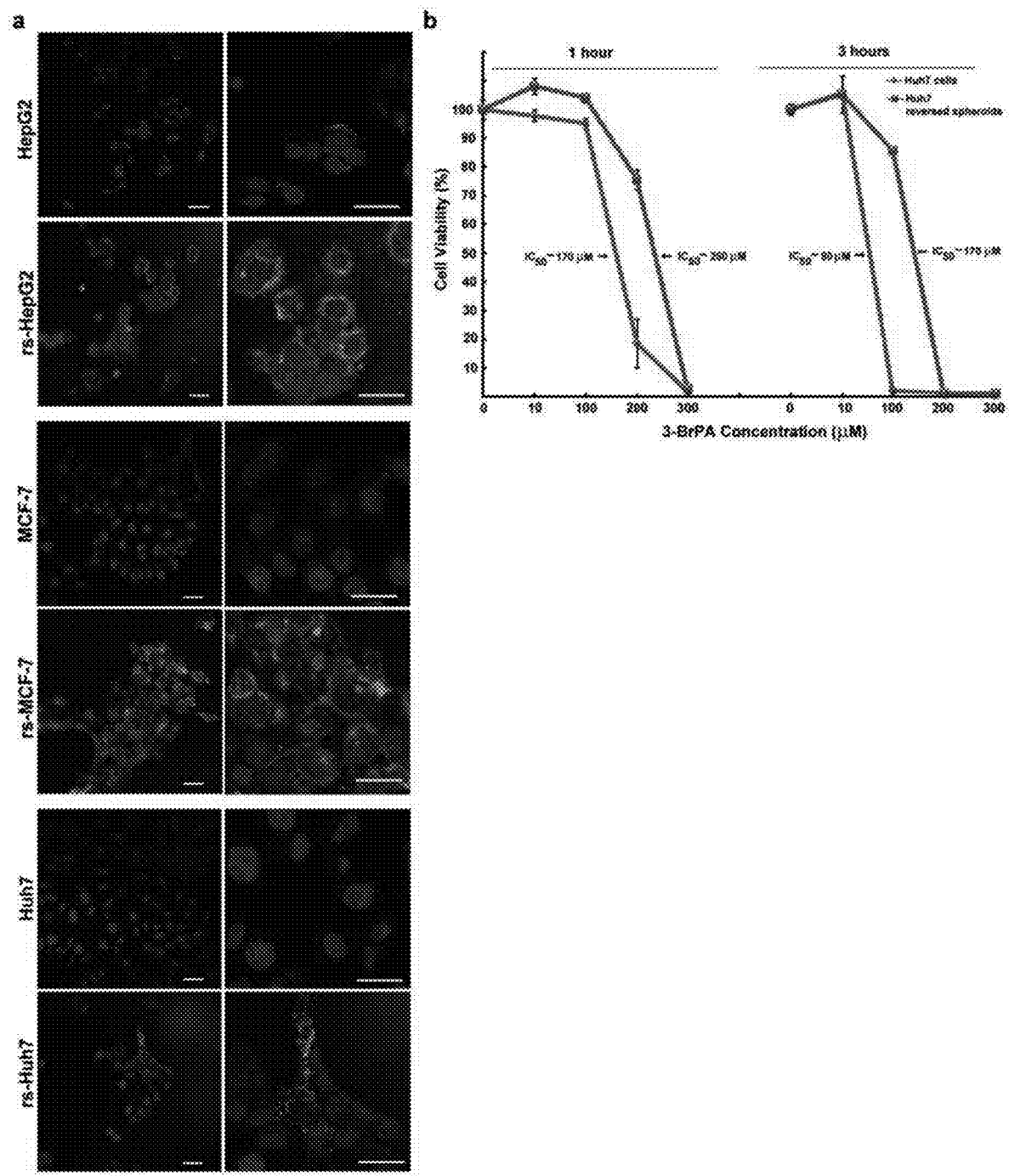
FIG. 7A-7B. Chemoresistance in rs-monolayer population.
Figure 13:
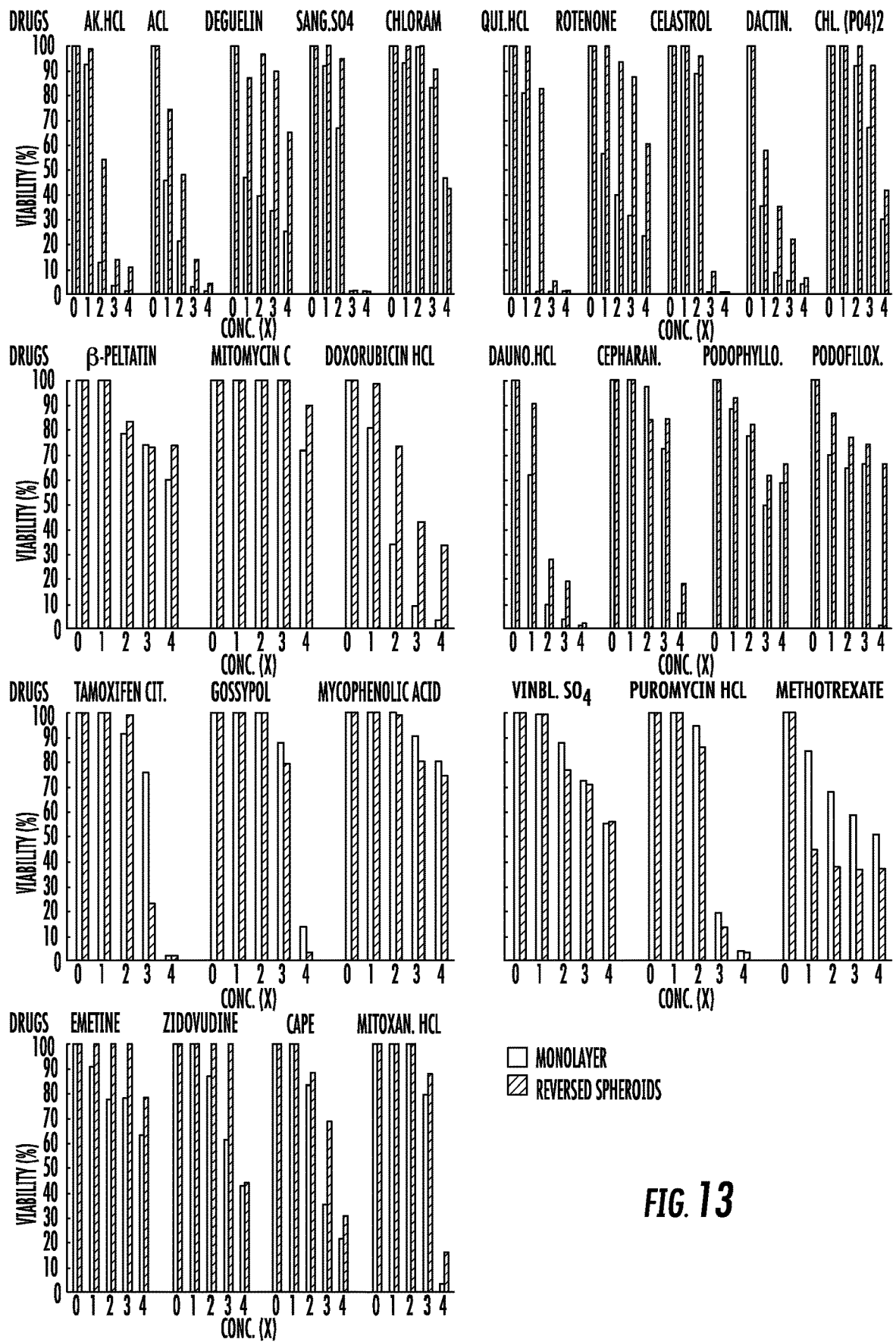
FIG. 13. Differential chemosensitivity of rs-monolayer cells. A comparative analysis of chemosensitivity of rs-monolayer and parental population of Huh7 cells.

Next we investigated if the metastatic phenotype exhibited by rs-monolayer also correlated with any differential sensitivity to anticancer agents. In accordance with the qPCR data (FIG. 2), the expression level of ABCG2, a regulator of drug-efflux that plays a pivotal role in chemoresistance, showed a marked increase in rs-monolayer (FIG. 7a). To validate that the increased expression of ABCG2 affects drug sensitivity we treated rs-monolayer and parental monolayer cells of luc-Huh7 to a glycolytic inhibitor, 3-bromopyruvate. The data show that the rs-monolayer cells require a higher concentration of drug indicating a decrease in sensitivity (FIG. 7b). Preliminary analysis of the chemosensitivity using BIOLOG's phenotypic microarray also confirmed marked variation in response to different anticancer agents (FIG. 13). Data showed out of 72 anticancer agents only 27 had any effect on any form of luc-Huh7 cells (parental or rs), in which parental monolayer cells were more sensitive to 21 agents while the reversed spheroid cells were more sensitive to only 6 agents. Thus, rs-population in general possesses differential drug sensitivity than the parental cell line.

Figures 8A, 8B, 8C, 8D:
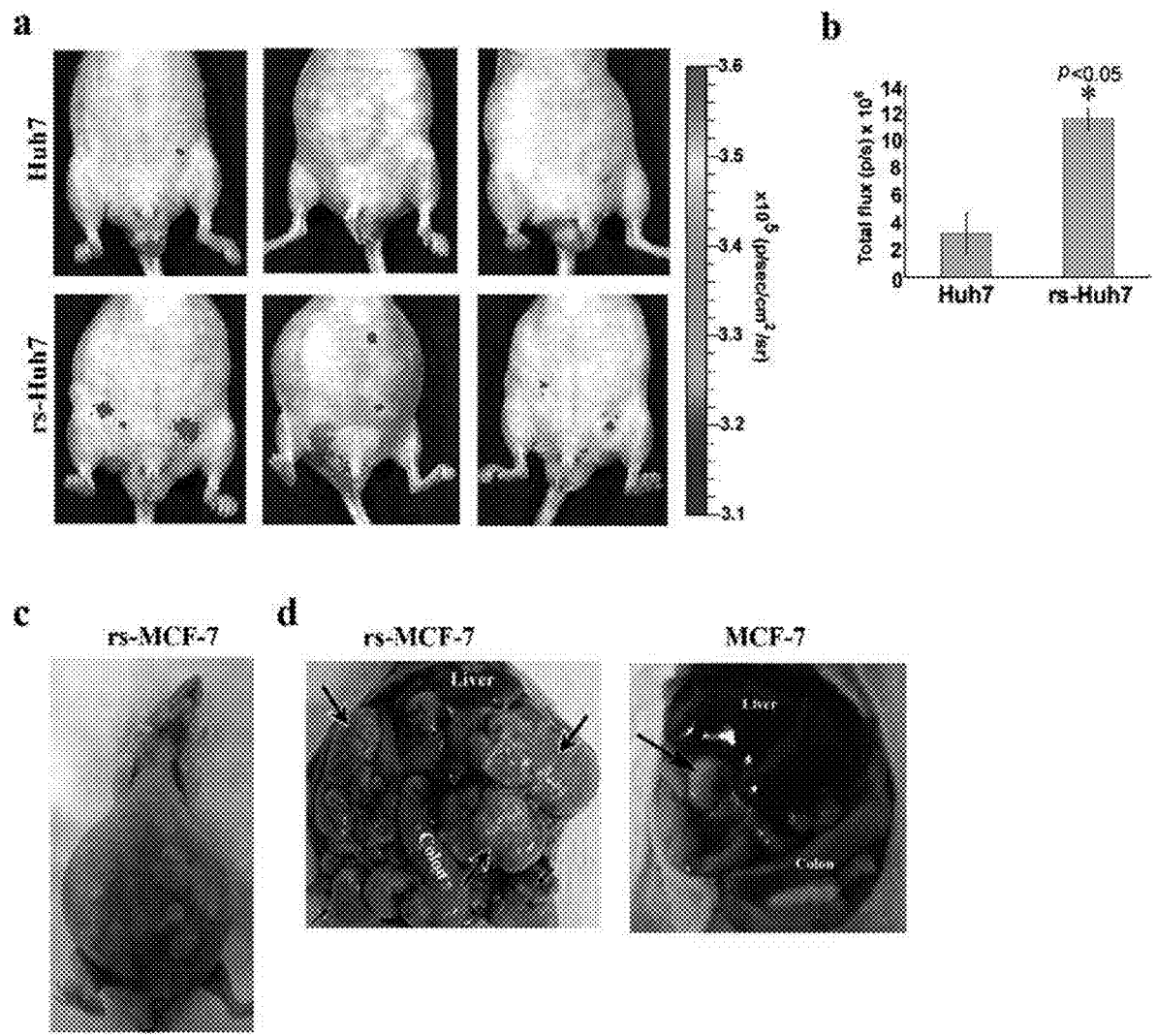
FIG. 8A-8D. In vivo evaluation of tumorigenicity of reverse-spheroid population and heterogeneous monolayer population.

Next we validated the tumor initiation capacity of rs-cells in vivo. Data from animal imaging showed that intraperitoneal injection of rs-monolayer formed multiple nodules compared to the parental cell line (FIG. 8). This demonstrated that rs-monolayer cells have higher seeding or tumor initiation capacity, a typical feature of metastatic cancer.

DISCUSSION

Results of the current study demonstrate that reversed-spheroid population possesses aggressive phenotypic characteristics such as invasion, cancer stem cell markers and chemoresistance. Clinically, these salient features are attributed to poor prognosis and therapeutic challenges. Although MCS of cancer cells have been known to possess these aggressive properties, until this report there is no documentation of the preservation or propagation of such malignant (metastatic, chemoresistant and cancer stem cell-like) phenotype after reversal into a monolayer. In other words, we demonstrate that the malignant (EMT, CSC, metastatic) characteristics of MCS are maintained even after the reversal of phenotype into a monolayer. Further this also indicates that the MCS generated by ultra-low attachment culture condition rather than using a supporting medium (e.g., matrix) in fact selected metastatic, aggressive cells. This is further supported by the observation that not all cells formed the MCS, and many of them did not survive the anchorage-independent condition resulting in cell death.

The reversal of MCS also circumvents some of the concerns related to spheroids under 3D culture. For example, the tumor spheroids have been known to develop chemical gradients (e.g., of oxygen, nutrients, and catabolites) at diameters between 200 and 500 µm with a central secondary necrosis typically established at sizes >500 µm. While this mimics an in vivo tumor, from the perspective of metastasis it remains unknown whether the central necrotic core and any chemical or oxygen gradients can impact any of the metastatic properties of these cells. Moreover, in vivo, tumor vasculature plays a pivotal role in the delivery of required nutrients, and this achieved through neo-angiogenesis. In fact, the angiogenic phenomenon of tumor cells is so prominent that angiogenic inhibitors including anti-VEGF molecules have been intensely pursued as potential therapeutics. In vitro, in the spheroids the lack of an angiogenic or vascular system confounds cellular characteristics especially under 3D, anchorage-independent culture condition. Thus, reversal of spheroid cells into a monolayer facilitates typical epithelial culture but with the integration of metastatic signatures. Further, EMT is one of the early steps of initiation of metastatic processes. As EMT is a critical determinant of tumor cell dissemination any 3D model of cancer cells should integrate the process of EMT. Thus our approach to develop MCS solely based on anchorage-independent growth without the use of support materials (e.g., collagen or matrigel) not only induces EMT but also minimizes any undesirable effects, if any, that could be related to the supporting matrices.

Several studies have demonstrated that CD133 positive cells have stem cell-like features in various cancers and it is increasingly evident that CSCs play a pivotal role in tumor metastasis. Similarly, CXCR4, a receptor for chemokine SDF1, has been suggested as a critical factor for the metastatic potential of CSCs and tumor invasion. The metastatic ability of CSCs has been attributed to the expression of transgelin as well. In fact, it is suggested that transgelin may replace the twist protein as a key regulator of TGF-beta signaling in at least Huh7 tumorigenic cells undergoing EMT. It is well known that EMT is characterized by the combined loss of epithelial cell junction proteins such as E-cadherin and the gain of mesenchymal markers such as vimentin. Besides, recent data also establish that most malignant cells transition from EMT, and such EMT driven cells are more invasive and resistant to therapy. Thus upregulation of multiple CSC markers and EMT genes in rs-monolayer indicate that the aggressive phenotype acquired during the generation of anchorage-independent MCS are preserved or maintained in the reversal process as well.

Chemoresistance is a common and frequently witnessed property of metastatic cancers. Clinically, as metastatic cells are known to be resistant to cancer therapies, we next investigated if the rs-monolayer has differential sensitivity to anti-cancer agents. Flow cytometry analysis further confirmed an increase in ABCG2 expressing cells (data not shown). Nevertheless, in vivo data unequivocally demonstrate that tumor initiation capacity of rs-monolayer cells is markedly higher than the parental population. In summary, the rs-monolayer incorporates clonogenic (colonies or spheroids) capacity, migratory and invasive properties along with chemoresistance suggestive of all the metastatic characteristics to investigate its biology and regulation. This in vitro model of metastasis could be valuable in understanding the molecular regulation of metastatic cascade which in turn could provide insights into the potential therapeutic targets.

Example 2

Metabolic Plasticity

Reverse-spheroid cells represent the recently included hall mark of cancer, i.e. metabolic reprogramming. Recently, Hanahan and Weinberg (144(5) CELL 646-74 (2011)) described the identification and inclusion of additional hallmarks of cancer. Metabolic reprogramming or altered energy metabolism is one of the hallmarks of cancer. In brief, the altered energy metabolism of cancer includes the propensity to consume enormous quantity of glucose and a preferential utilization of it by glycolysis, irrespective of oxygen availability. Unlike normal or noncancerous cells which use mitochondrial oxidation for glucose metabolism, cancer cells with tumorigenic potential have been known to rely on glycolysis, hence up-regulate the level of glycolytic enzymes. See Ganapathy-Kanniappan S. and Geschwind J. F., 12 MOL. CANCER 152 (2013).

Here, we investigated if the initiation of anchorage-independent growth (also known epithelial mesenchymal transition or EMT) selects cancer cells with the metabolic plasticity (ability to upregulate glycolytic enzymes). Real-time qPCR analysis showed that cancer cells grown under ultra-low attachment condition (anchorage-independent growth) exhibit up-regulation of glycolytic enzymes (FIG. 14). Importantly, such up-regulation of glycolytic enzymes also correlated with the induction of proto-oncogene, c-jun. Furthermore, even after the spontaneous reversal of spheroid cells into monolayer (epithelial phenotype), although there was a reversal in the level of these enzymes, significantly, they all showed higher expression level than the heterogeneous (parental) monolayer population (arrow indicates the trend). Thus the rs-monolayer cells represent the metabolic plasticity cells with higher glycolytic capacity which is one of the hallmarks of cancer.

We claim:

1. A method for generating an in vitro model of metastatic cancer comprising the steps of:
   (a) culturing cancer cells under non-adhesive conditions to produce spheroid cells via anchorage independent growth, wherein the cancer cells undergo an epithelial to mesenchymal transition during the generation of spheroids from a monolayer;
   (b) isolating the spheroid cells; and
   (c) culturing the spheroid cells under adhesive conditions to reverse the spheroid cells into monolayer cells, wherein the cells undergo a mesenchymal to epithelial transition and display a metastatic phenotype.

2. The method of claim 1, wherein the culturing step to produce spheroid cells is performed without extracellular matrix substances or chemical chelating agents that promote spheroid formation.

3. A method for preparing reversible spheroid cancer cells comprising the steps of:
   (a) culturing adherent cancer cells under non-adhesive conditions sufficient to form spheroid cells via anchorage independent growth, wherein the cancer cells undergo an epithelial to mesenchymal transition during the generation of spheroids from a monolayer; and
   (b) culturing the spheroid cells under adhesive conditions to reverse the spheroid cells into monolayer cells, wherein the reversed-spheroid monolayer cells undergo a mesenchymal to epithelial transition and display a metastatic phenotype.

* * * * *